US012631629B2

(12) United States Patent
Mohanty et al.

(10) Patent No.: US 12,631,629 B2
(45) Date of Patent: May 19, 2026

(54) DEVICE AND METHODS FOR RAPID DETECTION OF TARGET ANALYTES IN A BIOLOGICAL SAMPLE

(71) Applicant: Ambient Biosciences, Inc., Ann Arbor, MI (US)

(72) Inventors: Pravansu S. Mohanty, Ann Arbor, MI (US); Zhuoran Wang, Ann Arbor, MI (US); Subhendu Das, Ann Arbor, MI (US); Yolanda Taverner, Ann Arbor, MI (US); Arun Reddy, Ann Arbor, MI (US); Pallavi Joshi, Ann Arbor, MI (US); Shruti Amle, Ann Arbor, MI (US); Jenny Mantyla, Ann Arbor, MI (US); Laura Bronsart, Ann Arbor, MI (US); Mary Retzlaff, Ann Arbor, MI (US)

(73) Assignee: Ambient Biosciences, Inc., Ann Arbor, MI (US)

( * ) Notice: Subject to any disclaimer, the term of this patent is extended or adjusted under 35 U.S.C. 154(b) by 748 days.

(21) Appl. No.: 17/907,109

(22) PCT Filed: Mar. 31, 2021

(86) PCT No.: PCT/US2021/025115
§ 371 (c)(1),
(2) Date: Sep. 23, 2022

(87) PCT Pub. No.: WO2021/202685
PCT Pub. Date: Oct. 7, 2021

(65) Prior Publication Data
US 2023/0104815 A1 Apr. 6, 2023

Related U.S. Application Data

(60) Provisional application No. 63/051,668, filed on Jul. 14, 2020, provisional application No. 63/002,873, filed on Mar. 31, 2020.

(51) Int. Cl.
*G01N 33/543* (2006.01)
*G01N 21/64* (2006.01)
*G01N 21/78* (2006.01)
*G01N 33/569* (2006.01)

(52) U.S. Cl.
CPC ... *G01N 33/54386* (2013.01); *G01N 21/6428* (2013.01); *G01N 21/78* (2013.01); *G01N 33/54346* (2013.01); *G01N 33/56983* (2013.01); *G01N 2021/6439* (2013.01); *G01N 2333/165* (2013.01); *G01N 2469/10* (2013.01); *G01N 2469/20* (2013.01)

(58) Field of Classification Search
None
See application file for complete search history.

(56) References Cited

U.S. PATENT DOCUMENTS

| | | | |
|---|---|---|---|
| 5,415,994 A | 5/1995 | Imrich | |
| 5,434,051 A | 7/1995 | Allard et al. | |
| 5,541,117 A | 7/1996 | Karl | |
| 7,393,697 B2 | 7/2008 | Charlton | |
| 8,003,407 B2 | 8/2011 | Zhou | |
| 10,408,829 B2 | 9/2019 | Dambinova | |
| 10,433,540 B2 | 10/2019 | Mohanty | |
| 2009/0162833 A1* | 6/2009 | Mertens | G01N 33/569 |
| | | | 436/514 |
| 2013/0309656 A1 | 11/2013 | Davis | |
| 2014/0212985 A1 | 7/2014 | Jacobs | |
| 2019/0200603 A1 | 7/2019 | Mohanty | |
| 2019/0376970 A1 | 12/2019 | Sambursky | |
| 2025/0171862 A1* | 5/2025 | Manohar | C12Q 1/6818 |

FOREIGN PATENT DOCUMENTS

| | | |
|---|---|---|
| CN | 1216677 A | 5/1999 |
| CN | 1340710 A | 3/2002 |
| CN | 207816989 U | 9/2018 |
| JP | A 1994011510 | 1/1994 |
| JP | A 1994509646 | 10/1994 |
| JP | 2007-524813 A | 8/2007 |
| JP | 2009-518636 A | 5/2009 |
| JP | 2017116537 A | 6/2017 |
| WO | 1998/00032 A1 | 1/1998 |
| WO | WO2002052263 A1 | 7/2002 |
| WO | WO2007098184 A2 | 8/2007 |
| WO | WO2015084458 A1 | 6/2015 |
| WO | WO2021209228 A1 | 10/2021 |

OTHER PUBLICATIONS

Li et al. (Journal of Biological Engineering, 2019, p. 1-12).*
Fung, K., et al., Development of enzyme-based bar code-style lateral-flow assay for hydrogen peroxide determination, Analytica Chimica ACTA, 634(1): 89-95, Feb. 16, 2009.
Lu, X., et al., Improved performance of lateral flow immunoassays for alpha-fetoprotein and vanillin by using silica shell-stabilized gold nanoparticles, Mocrochimica ACTA, 186(1): 1-7 Dec. 4, 2018.
Parolo, C., et al., Enhanced lateral flow immunoassay using gold nanoparticles loaded with enzymes, Biosensors and Electronics, 40(1): 412-416, Jun. 30, 2012.
Lan, J., et al., Structure of the SARS-COV-2 spike receptor-binding domain bound to the ACE2 receptor, Nature, 581 (7807): 215-220, Mar. 30, 2020.
Shen, Y., et al., Signal-Enhanced Lateral Flow Immunoassay with Dual Gold Nanoparticle Conjugates for the Detection of Hepatitis B Surface Antigen, ACS Omega, 4(3): 5083-5087, Mar. 8, 2019.

* cited by examiner

*Primary Examiner* — Agnieszka Boesen
(74) *Attorney, Agent, or Firm* — Weston R. Gould; Dinsmore & Shohl LLP

(57) ABSTRACT

Provided herein is a rapid lateral flow device for detection of a target analyte in a liquid biological sample comprising a membrane strip, the membrane strip including: a matrix; a conjugate pad having at least one reporter vitrified into the matrix; one or more test sites including a covalently or electrostatically bound capture agent vitrified into or onto the matrix; and, optionally, a control line including one or more capture agents vitrified into or onto the matrix. Also provided are methods of rapid detection of a target analyte in a liquid biological sample.

20 Claims, 25 Drawing Sheets

FIG. 5

Channel 2: Fibers here provide the substrate to vitrify the detection antibody/fluorophore conjugate, but the antibodies aren't bonded to it, so that they can be released upon rehydration. Once the separator is pulled away, they form the sandwich with the capture antibody/antigen conjugate in Channel 1 and result in fluoroscence Diluent Serum Separator Channel 1: Fiber inside the capillary channel (draws the serum in) having covalently bonded capture antibody (the fiber itself doesn't have any affinity towards protein binding and hence eliminates contamination issues) is vitrified for ambient temperature stability. The surface area and porosity reduces perfusion time to 10 minutes Channel 1: Fluoroscent image after rehydration and release Channel 2: Fluoroscent image-VGEF detection Bright field image

FIG. 7C
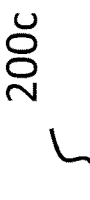
200c
230
220
210
FIG. 7B
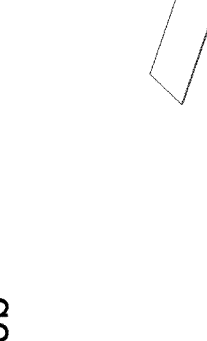
200b
230
220
210
FIG. 7A
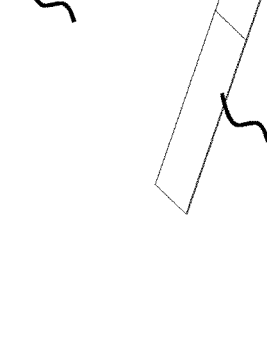
200a
230
220
210
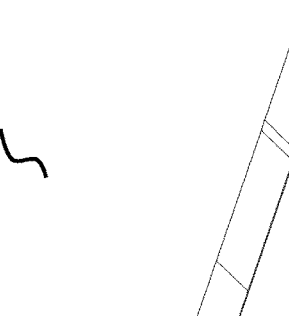

FIG. 14

FIG. 19
Lines are visible After TMBM Substrate addition
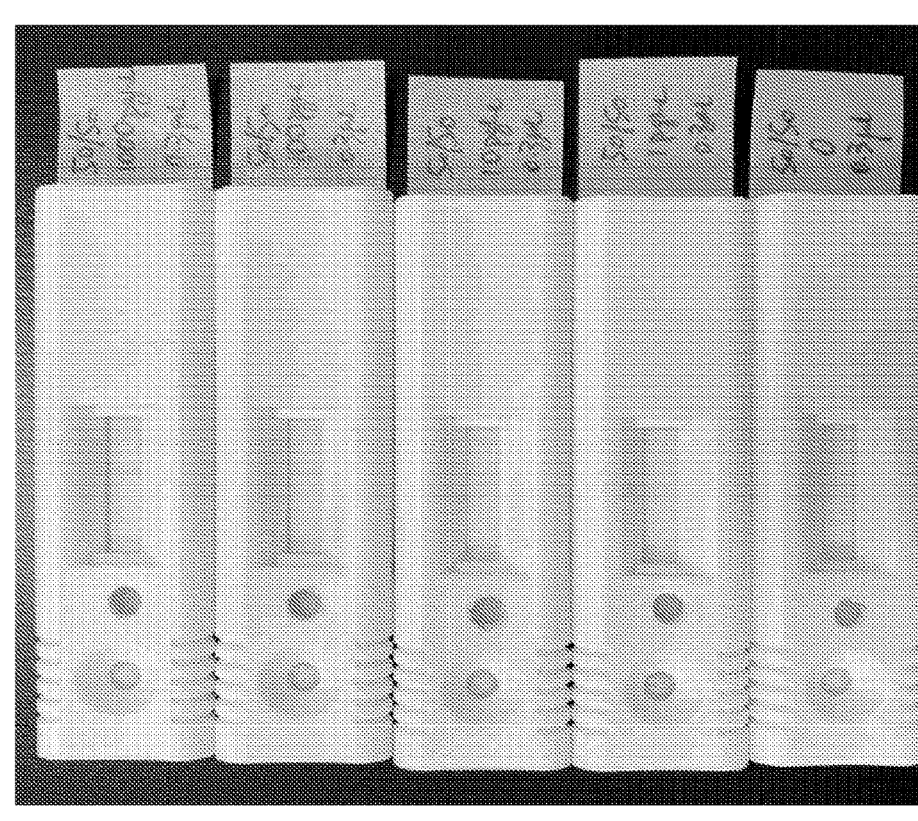
Prior to Substrate addition no line is visible
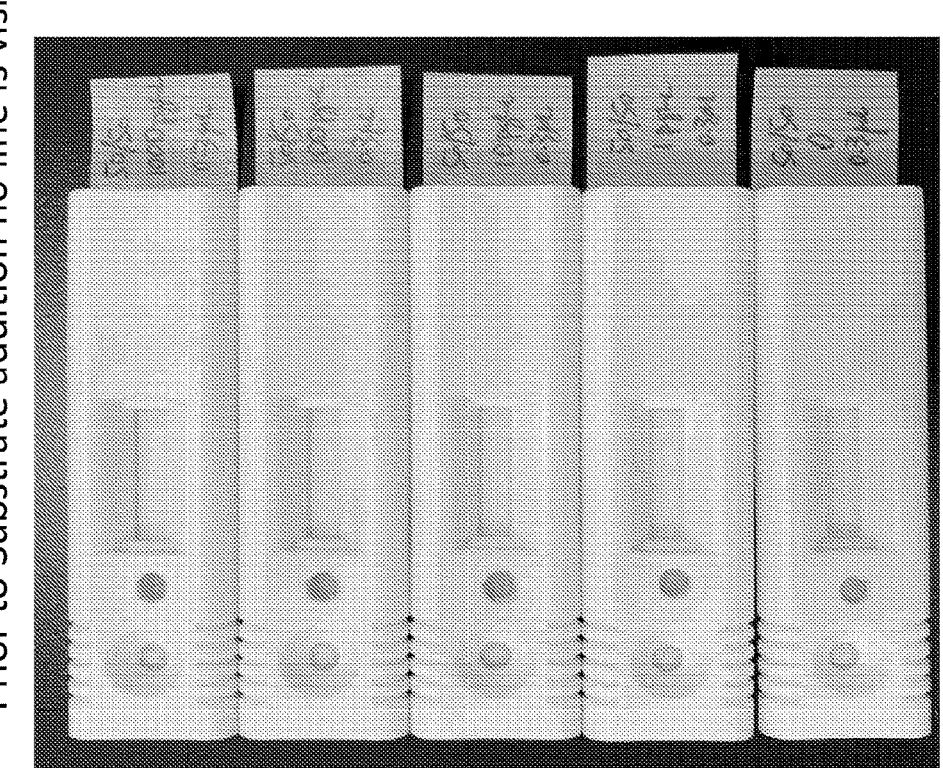

FIG. 22

DEVICE AND METHODS FOR RAPID DETECTION OF TARGET ANALYTES IN A BIOLOGICAL SAMPLE

CROSS REFERENCE TO RELATED APPLICATIONS

This application is a U.S. National Stage under 35 U.S.C. § 371 of international application number PCT/US2021/025115 filed Mar. 31, 2021, and which depends from and claims priority to U.S. Provisional Application No. 63/002,873 filed Mar. 31, 2020 and U.S. Provisional Application No. 63/051,668 filed Jul. 14, 2020, the entire contents of each of which are incorporated herein by reference.

FIELD

This disclosure relates to rapid diagnostic devices and methods for detecting the presence or absence of one or more target analytes in a biological sample.

BACKGROUND

Standard serological diagnostic methods for detecting the presence or absence of antibodies, enzymes or pathogens in a biological sample often require cold-chain shipping and storage, specialized equipment, and skilled workers to perform complex laboratory procedures. Methods such as enzyme linked immunosorbent assay (ELISA), polymerase chain reaction, or bead-based profiling kits (e.g., Luminex® assays) require a minimum of three or more hours to obtain test results and accuracy may suffer due to sample degradation or contamination, leading to false positives or negatives. When the number of test samples overwhelms laboratory staff and resources, for example during pandemic or epidemic events, patients may wait days or even weeks to obtain test results. Lengthy delays in receiving accurate test results may facilitate further transmission of the pathogen, thereby resulting in further overwhelmed medical facilities and greater risk of compromised patient care.

A need persists for a rapid, robust assay for the detection of one or more analytes, including antibodies or pathogens, in a biological sample.

SUMMARY

The following summary is provided to facilitate an understanding of some of the innovative features unique to the present disclosure and is not intended to be a full description. A full appreciation of the various aspects of the disclosure can be gained by taking the entire specification, claims, drawings, and abstract as a whole.

Provided herein are devices and methods for the rapid detection of one or more target analytes in a liquid biological sample, whereby the assay materials do not require cold-chain storage, are robust and preserve activity even after prolonged storage at elevated temperatures of 55° C. or greater for weeks or months, and may be directly used at the point-of-care, optionally without complex detection instrumentation other than a human eye. The presently disclosed devices include a membrane that includes a vitrified matrix comprising capture agents that may or may not be optionally covalently bound to the matrix and that may or may not themselves include a detectable label (e.g. enzyme), and one or more desired reporter molecules (e.g. antibodies, nucleic acids, etc.) optionally vitrified to the matrix or to another matrix layer of the device, whereby the vitrified matrix and/or other matrix layer may be rehydrated upon contact with a liquid biological sample, such that the reporter is released, the target analyte in the sample binds the capture agent and the reporter, and presence or absence of the target analyte is detected. In some aspects, the device and methods set forth herein provide qualitative and/or quantitative detection results. The disclosed devices are time and temperature stable and do not require cold-chain shipping or storage. Further, the disclosed devices and methods advantageously permit rapid, point-of-care diagnostic results in about 20 minutes or less according to some aspects.

In some aspects, a lateral flow immunoassay device includes a membrane strip is provided, the membrane strip comprising: a matrix; a conjugate pad includes at least one reporter that may include one or more detectable labels, optionally an antigen or antibody for a target analyte the antigen or antibody optionally including a detectable label or labeling molecule, the reporter vitrified into the matrix; one or more test regions optionally comprising a covalently bound capture antibody or aptamer specific for the type of target analyte, the covalently bound capture antibody or aptamer vitrified into the matrix; and, optionally, a control region including one or more second capture agents vitrified into the matrix, the control region second capture agents suitable for binding a control reagent that may optionally be further included in the conjugate pad.

These and other objects, features, and aspects of the present disclosure are further understood by reference to the drawings and detailed description set forth herein.

BRIEF DESCRIPTION OF THE DRAWINGS

The aspects set forth in the drawings are illustrative and exemplary in nature and not intended to limit the subject matter defined by the claims. The following detailed description of the illustrative aspects can be understood when read in conjunction with the following drawings, where like structure is indicated with like reference numerals and in which:

FIG. 5 illustrates an exemplary aspect of a device according to the disclosure, wherein a removable separator layer is disposed between two channels.

FIG. 7A illustrates an exemplary aspect of a lateral flow membrane strip according to the present disclosure.

FIG. 7B illustrates an exemplary aspect of a lateral flow membrane strip according to the present disclosure.

FIG. 7C illustrates an exemplary aspect of a lateral flow membrane strip according to the present disclosure.

FIG. 14 illustrates an exemplary multi-strip lateral flow assay according to the present disclosure.

FIG. 19 illustrates a device provided according to some aspects as provided herein processed using recombinant SARS-CoV-2 S protein as a sample and detected with to less than 10 pg/ml.

FIG. 22 illustrates a device provided according to some aspects as provided herein comparing the direct bonding of capture agent to a test site (A) with precoating the test site with a molecule that binds the capture agent (B).

DETAILED DESCRIPTION

Figure 1:
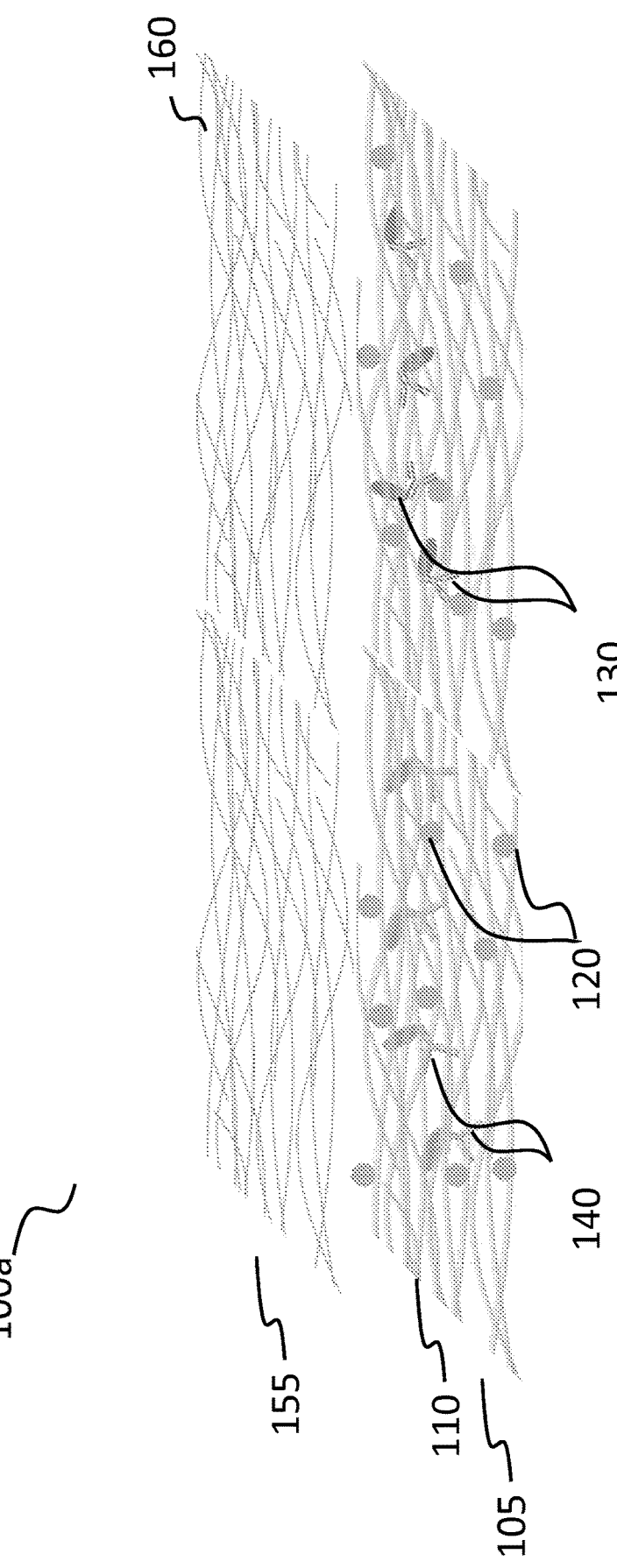
FIG. 1 illustrates an exemplary aspect of a device according to the disclosure, wherein capture antigen and reporter antibodies are vitrified into the membrane layer matrix.

Provided herein are devices and methods for the rapid diagnostic detection of a target analyte in a liquid biological sample. As described in detail herein, vitrification of a bound capture agent, and optionally a reporter, into a matrix, permits rapid reconstitution of the matrix upon contact with a liquid biological sample, thereby releasing the reporter and capture agent and enabling rapid, point-of-care immunoassay detection of the target analyte, without the need for cold-chain shipment or storage. It was found that particular molecules can be embedded in, covalently or electrostatically attached to, or otherwise associated with a membrane and subjected to a vitrification process that effectively stabilizes the molecule(s), thereby preserving their activity despite subsequent storage in otherwise harsh conditions and negating the need for the usual cold-chain storage processes. All analytical materials may optionally be vitrified in or with a device as provided herein such that reconstitution with a liquid biological sample (e.g. blood, plasma, serum, saliva, bronchoalveolar lavage fluid, sputum, nasal secretion, skin secretion, buffer, water, or other liquid containing or being a biological sample or portion thereof) or other liquid will reconstitute the vitrified materials with little or no loss of activity, thereby providing a robust assay system for detection of one or more analytes that may or may not be present in the biological sample.

Detection of the presence of infectious agents (as one example of a target analyte) in a subject optionally a human subject, presents numerous challenges to the diagnostician. For example, detection of the viral agent itself may be difficult, particularly if the infection is recent so that viral load is low, or if an active infection has resolved but it is desired to know if infection previously occurred or if a subject has a persistent immunity. Viral infection may produce antibodies to the virus within the subject. Detection of these antibodies may provide information related to prior or current exposure to the virus. As a non-limiting example, infection by a Betacoronavirus, such as human coronaviruses SARS-CoV (the causative agent of Severe Acute Respiratory Syndrome, or SARS) and MERS-CoV (the causative agent of Middle Eastern Respiratory Syndrome, or MERS), presents several challenges due to the rise of new strains. Detection of these new strains in the rapidly transmissible novel coronavirus SARS-CoV-2 (the causative agent of COVID-19 disease, or COVID-19) has required the development of diagnostic assays specific for this new virus.

The devices and methods as provided herein provide rapid, reproducible, and optionally quantifiable detection of one or more target analytes in a biological sample. As provided herein, a device includes a housing and a substantially dry membrane layer within the housing, the membrane layer including a first matrix and a capture agent vitrified into or onto the first matrix at a first test site. The device may be in the form of a lateral flow assay wherein a liquid biological sample (or target analyte in liquid) is applied at a sample application site and the liquid wets the membrane and travels toward one or more test sites at a position other than the sample application site. The liquid in between the sample application site and the test site may wet and rehydrate a reporter and/or a capture agent (or other desired molecule) that can effectively localize the target analyte at the test site to thereby provide detection of the presence or absence of the target analyte within the biological sample.

In some aspects, a device is a lateral flow device including a substantially dry membrane, the membrane including: a matrix; a conjugate pad comprising one or more test regions comprising a covalently or electrostatically bound capture agent (e.g. antigen, aptamer, nucleotide, or antibody) vitrified into the matrix; optionally at least one reporter antibody vitrified into the matrix; and optionally a control region comprising one or more second capture agents vitrified into the matrix.

In some aspects, a rapid diagnostic device for detecting an analyte of interest in a liquid biological sample is provided, comprising: a membrane layer, the membrane layer comprising a first matrix, a capture agent vitrified into the first matrix, and at least one reporter vitrified into the first matrix. Optionally, the device further comprises a screen layer disposed on or otherwise in contact with the membrane layer. The screen layer, when present, may include a second matrix, and is configured to function as a filter that substantially captures and sequesters contaminants (e.g., molecules other than the analyte of interest) in a liquid biological sample.

In some aspects, a rapid diagnostic device for detecting an analyte of interest in a liquid biological sample is provided, comprising: a membrane layer, the membrane layer comprising a first matrix and a capture agent vitrified into the first matrix; and a screen layer disposed on or otherwise in contact with the membrane layer, the screen layer including a second matrix configured to function as a filter that substantially captures and sequesters contaminants in the liquid biological sample, and optionally at least one reporter vitrified into the first matrix, second matrix, or both.

In some aspects, a rapid diagnostic device for detecting an analyte of interest in a liquid biological sample is provided, comprising: a membrane layer, the membrane layer comprising a first matrix and a capture agent vitrified into the first matrix; and a substantially dry substrate membrane including a substrate vitrified into or onto the substrate membrane, wherein the substrate membrane is associated with the housing and configured to be contacted with the membrane layer when desired, optionally after the membrane layer is wetted with a liquid, optionally from a liquid biological sample alone or in conjunction with a further wetting agent.

A membrane layer or the entire device as provided herein is optionally substantially dry. "Substantially dry" is defined as having a Moisture Residue Ratio (grams H2O/grams dry weight) of 0.1 or less, optionally, 0.05 or less, optionally 0.04 or less, optionally 0.03 or less, optionally 0.02 or less, optionally 0.01 or less.

"Amorphous" or "glass" refers to a non-crystalline material in which there is no long-range order of the positions of the atoms referring to an order parameter of 0.3 or less. Transformation of a liquid into a vitreous solid occurs at the glass transition temperature Tg. In some aspects, the vitrification medium may be or form an amorphous material. In other aspects, the biological material may be amorphous material.

"Glass transition temperature" means the temperature above which material behaves like liquid and below which material behaves in a manner similar to that of a solid phase and enters into amorphous/glassy state. This is not a fixed point in temperature, but is instead variable dependent on the timescale of the measurement used. In some aspects, glassy state may refer to the state the biological composition enters upon dropping below its glass transition temperature. In other aspects, the glassy state may refer to the state the vitrification mixture and/or vitrification agent enters upon dropping below its glass transition temperature. In yet other aspects, the glassy state may have the mechanical rigidity of a crystal or gel, but the random disordered arrangement of molecules that characterizes a liquid.

"Crystal" means a three-dimensional atomic, ionic, or molecular structure consisting of one specific orderly geometrical array, periodically repeated and termed lattice or unit cell.

"Crystalline" means that form of a substance that is comprised of constituents arranged in an ordered structure at the atomic level, as opposed to glassy or amorphous. Solidification of a crystalline solid occurs at the crystallization temperature Tc.

"Vitrification" as used herein, is a process of converting a material into an amorphous material. The amorphous solid may be free of any crystalline structure.

"Vitrification mixture" as used herein, means a heterogeneous mixture of biological material(s) and a vitrification medium containing one or more vitrification agents, optionally a lysing agent, and optionally other materials.

"Biological material" or a "biological sample" as used herein, refers to materials that may be isolated or derived from a living organism(s). Examples of biological materials include, but are not limited to proteins (e.g. enzymes, or non-enzymatically functional proteins), cells, tissues, organs, cell-based constructs, saliva or fraction thereof, blood or fraction thereof, nucleic acids, or combinations thereof. In some aspects, biological material may refer to mammalian cells. In other aspects, biological material may refer to human mesenchymal stem cells, murine fibroblast cells, white blood cells, red blood cells, blood platelets, bacteria, viruses, mammalian cells, liposomes, enzymes, tissues (e.g. intestine, liver, neuronal, or other), or combinations thereof. In other aspects, biological material may refer to reproductive cells including sperm cells, spermatocytes, oocytes, ovum, embryos, germinal vesicles, or combinations thereof. In other aspects, biological material may refer to whole blood, red blood cells, white blood cells, platelets, blood plasma, blood serum, saliva, gastric aspirate, nasal fluid, algae, fungi, or combinations thereof.

"Vitrification agent" as used herein, is a material that forms an amorphous structure, or that suppress the formation of crystals in other material(s), as the mixture of the vitrification agent and other material(s) cools or desiccates. The vitrification agent(s) may also provide osmotic protection or otherwise enable cell survival during dehydration. In some aspects, the vitrification agent(s) may be any water soluble solution that yields a suitable amorphous structure for storage of biological materials. In other aspects, the vitrification agent may be imbibed within a cell, tissue, or organ.

"Storable," "storage," or "storage-stable" as used herein, refers to a biological material's ability to be preserved and remain viable for use at a later time.

"Above cryogenic temperature," as used herein, refers to a temperature above −80° C. Room temperature, as used herein, refers to a temperature range from greater than or equal to 18° C. to less than or equal to 37° C.

"Hydrophilic," as used herein, means attracting or associating preferentially with water molecules. Hydrophilic materials with a special affinity for water, maximize contact with water and have smaller contact angles with water.

"Hydrophobic," as used herein, means lacking affinity for water. Materials that are hydrophobic naturally repel water, causing droplets to form, and have small contact angles with water.

"Ambient temperature," as used herein, refers to a temperature of from greater than or equal to about 16° C. and less than or equal to about 30° C.

"Liquid biological sample," as used herein, refers to a liquid sample that may contain a target analyte of interest. In aspects, the liquid biological sample is obtained from a subject, illustratively a human patient. In aspects, the subject is suspected of having a disease or condition, such as SARS-CoV-2 infection (i.e., COVID-19 disease), or any other infectious disease, such as influenza or other viral, bacterial, or fungal condigion, or the like. The liquid biological sample may be any sample capable of flowing through the matrices described herein and potentially harboring the analyte of interest. In some aspects, the liquid biological sample comprises saliva, blood, serum, plasma, bronchoalveolar lavage fluid, sputum, nasal fluid, skin secretions, or combinations thereof.

As used herein, a "subject" is an animal, optionally human, non-human primate, equine, bovine, murine, ovine, porcine, rabbit, or other mammal.

The devices and methods as provided herein may be used to detect the presence or absence of a target analyte within a biological sample. A target analyte may be any biological material. Optionally, a target analyte is a virus or portion thereof. In other aspects a target analyte may be a bacteria or portion thereof. Optionally, a target analyte may be a protein, optionally an enzymatically active protein. An exemplary virus used and exemplified throughout this disclosure for exemplary purposes alone is a human coronavirus. It is appreciated the devices and methods as provided herein are equally described with respect to any other virus, bacteria, fungus, or portion thereof. Human coronaviruses (HCoVs) are positive-sense, long (30,000 bp) single-stranded RNA viruses. HCoVs are characterized by structural proteins such as spike (S), nucleocapsid (N), membrane glycoprotein (M), and envelope (E), in addition to non-structural proteins, such as proteases (nsp3 and nsp5), helicase (nsp13), and RNA dependent RNA polymerase (RdRp, nsp12). It is known that the spike protein is a crucial recognition factor for virus attachment and entry into host cells. This disclosure provides devices and methods that can specifically detect the presence or absence of any infectious agent or other target analyte in a specific and robust system. In some aspects, this system is applied to detection of one or more HCoVs, optionally SARS-CoV-2.

A capture agent as used herein is optionally an antigen, enzyme, antibody or aptamer that binds, optionally selectively binds a target analyte. In some aspects, a capture agent is an antibody. Optionally a capture agent is an aptamer. Optionally, a capture agent is an antigen optionally in the form of a protein, nucleic acid or fatty material. Optionally, a capture agent is an enzyme. Optionally, a capture agent is an antibody such as an antibody specific for a target analyte, and optionally recognizing a binding site on the target analyte that differs from the binding site of a reporter.

Optionally, a capture agent is an antigen, such as an antigen that may be specifically recognized by an antibody as a target analyte wherein the antibody may be specific for an infectious agent within a biological sample the presence of which indicates the presence of or historical presence of the infectious agent within the subject. In other aspects, a capture agent is an aptamer raised or selected against one or more target analytes.

Recognition of a target analyte may be by forming a sandwich between a capture agent, a target analyte, and a reporter, whereby both the capture agent and the reporter bind the target analyte such that the target analyte is sequestered to the position of the capture agent and the reporter may emit or create a signal that is observable to identify the presence of the target analyte bound to the capture agent. It is appreciated that the devices and methods as provided herein may also be used in a competitive type assay such that the presence of a target analyte prevents association (e.g. competes) between a reporter and a capture agent to thereby detect the presence of a target analyte in a biological sample by the absence of signal at a test site.

A target analyte of interest is optionally a virus or portion thereof, an antibody directed to one or more protein molecules that are present on the surface of a virus, or viral protein or antigen. Optionally, the may be an enveloped virus, optionally from the group of Arenaviridae, Herpesviridae, Retroviridae, Coronaviridae, Poxviridae, Togaviridae, Flaviviridae, Bunyaviridae, Filoviridae, Orthomyxoviridae, Paramyxoviridae or Rhabdoviridae. The Coronaviridae can be selected a Colacovirus, Decacovirus, Duvinacovirus, Luchacovirus, Minacovirus, Minunacovirus, Myotacovirus, Nyctacovirus, Pedacovirus, Rhinacovirus, Setracovirus, Soracovirus, Sunacovirus, Tegacovirus, Embecovirus, Hibecovirus, Merbecovirus, Nobecovirus, Sarbecovirus, Brangacovirus, Brangacovirus, Igacovirus, Andecovirus, Buldecovirus, or Herdecovirus. Optionally, the Coronaviridae is a Betacoronavirus, optionally a Severe acute respiratory syndrome-related coronavirus, optionally a Severe acute respiratory syndrome coronavirus (SARS-CoV) or a Severe acute respiratory syndrome coronavirus 2 (SARS-CoV-2), or other related member. Optionally an Arenaviridae can be a Lassa virus, Junin virus or lymphocytic choriomeningitis virus (LCMV). Optionally, a Herpesviridae can be a herpes simplex virus, hepatitis B virus, varicella-zoster virus, cytomegalovirus or Epstein-Barr virus. Optionally, a Retroviridae can be the human immunodeficiency virus or the human T-lymphotropic virus. Other exemplary viral target agents or that cause a subject to produce antibodies against include but are not limited to smallpox virus, rubella virus, hepatitis C virus, Zika virus, West Nile virus, dengue virus, yellow fever virus, TBE virus, Semliki Forest virus, Rift Valley fever virus, sandfly fever virus, Hantaan virus, Marburg virus, Ebola virus, influenza virus A, influenza virus B, influenza virus C, Nipah virus, human parainfluenza virus, measles virus, mumps virus, vesicular stomatitis virus, or rabies virus.

In some aspects, a virus is a non-enveloped virus, optionally Adenoviridae, Polyomaviridae, Papillomaviridae, Hepeviridae, or rhinovirus.

Optionally, a viral target analyte is a HCoV, optionally SARS-CoV-2.

In some aspects as provided herein, an antibody target analyte in a biological sample from a subject may be detected. In some aspects such as the detection of a viral infection of a subject may include detection of an antibody produced against the virus by the subject. A capture agent specific for an antibody that selectively binds a virus, bacterial, fungi or other infections agent may be covalently or electrostatically attached to the matrix of a membrane at a test site or region, such as a test line or well. An anti-IgG, anti-IgM, anti-IgA, or other reporter bound to or including a reporter molecule (e.g. fluorophore, chromophore, nanoparticle, enzyme, or other detection agent) is also included in a matrix at or near a sample deposition area.

The capture agent and optional reporter molecules are vitrified in the matrix. Contact of the matrix with a liquid biological sample will reconstitute the vitrified molecules. Any target analytes in the biological sample are bound to the reporter and transferred along the membrane, optionally by capillary or other action to a test region whereby any capture agent specific for the target analyte of interest localizes the analyte such that the presence of the analyte may be detected by the reporter also thereby localized at the test region. As a control, covalently or electrostatically bound control capture agents in a control strip may be downstream of the test region, allowing for a positive control such as by detecting the movement of the capture agent past the test region. A positive result is achieved by detection of the signal emitted from the reporter localized in the test region.

In some aspects, a device and method allow for the detection of the presence of an infections agent itself. As a non-limiting example, a capture agent that specifically binds a viral coat protein, illustratively a spike protein or nucleocapsid protein, or a portion thereof is covalently or electrostatically attached to the matrix of a membrane at a test region, such as a test line or well. A reporter antibody that also binds the infectious agent at a region differing from the capture antibody is provided whereby the reporter antibody bound to a reporter molecule (e.g. fluorophore, chromophore, enzyme, or other detection) is also included in a matrix at or near a sample deposition area, or is maintained separate from the system prior to sample application. Contact of the matrix with a liquid biological sample will reconstitute the vitrified molecules. Any target analytes in the biological sample are bound to the reporter antibodies and transferred along the membrane, optionally by capillary or other action to a test region whereby any capture antibodies specific for the target analyte of interest localizes analyte to the test region. As an optional control, covalently or electrostatically bound antibodies that may bind the reporter antibody in a control strip are downstream of the test region, allowing for a positive control. A positive result is achieved by detection of the signal emitted from or generated by the reporter localized in the test site.

A device as provided herein incudes a matrix into or onto which one or more capture agents may be associated at one or more locations. Illustrative examples of matrix materials include polymers, optionally including but not limited to, collagen, elastin, hyaluronic acid and derivatives, sodium alginate and derivatives, chitosan and derivatives, gelatin, starch, cellulose polymers (for example, nitrocellulose (e.g. Sartorius CN95), methylcellulose, hydroxypropylcellulose, hydroxypropylmethylcellulose, carboxymethylcellulose, cellulose acetate phthalate, cellulose acetate succinate, hydroxypropylmethylcellulose phthalate), poly(diol citrate) (e.g., poly(octanediol citrate), etc.), casein, dextran and derivatives, poly(caprolactone), poly(hydroxyl acids), poly (L-lactide) poly(D,L lactide), poly(D,L-lactide-co-glycolide), poly(L-lactide-co-glycolide), copolymers of lactic acid and glycolic acid, copolymers of ε-caprolactone and lactide, copolymers of glycolide and ε-caprolactone, copolymers of lactide and 1,4-dioxane-2-one, polymers and copolymers that include one or more of the residue units of the monomers D-lactide, L-lactide, D,L-lactide, glycolide, s-caprolactone, trimethylene carbonate, 1,4-dioxane-2-one or 1,5-dioxepan-2-one, poly(glycolide), poly(hydroxybutyrate), poly(alkylcarbonate) and poly(orthoesters), polyesters, poly(hydroxyvaleric acid), polydioxanone, poly(ethylene terephthalate), poly(malic acid), poly(tartronic acid), polyanhydrides, polyphosphazenes, poly(amino acids), and copolymers of the above polymers as well as blends and combinations of the above polymers. Illustratively such polymers are as described in U.S. Patent Application Publication No. 2018/0125990 and references as cited therein including *Polymers in Controlled Drug Delivery* (Illum, L. & Davids, S. S., eds., Wright, Bristol 1987); Arshady, *J. Controlled Release* 17:1-22 (1991); Pitt, *Int. J. Phar.* 59:173-96 (1990); Holland et al., *J. Controlled Release* 4:155-80 (1986). In a specific aspect, the first and second matrices are independently selected from the group consisting of collagen, polycaprolactone, polylactic acid, poly(lactic-co-glycolic acid), or combinations thereof.

Optionally, a matrix is present in the form of a fibrous random or ordered mesh that defines channels or other continuous or discontinuous routes of access for a fluid or a target analyte. Optionally, a matrix is in the form of a non-woven fibrous mesh with high porosity (e.g. greater than 50% by volume).

Polymers that may be used in a matrix herein optionally can be formed into a porous mesh, such as in the form of a filter, symmetric mesh, or other such porous sheet-like material. Illustratively, a polymer is formed into a fibrous network such as by methods that include electrospinning. In electrospinning, desired polymers are placed in a desired solvent (e.g. 2,2,2-trifluoroethanol (TFE) or hexafluoroisopropanol (HFIP)) and subjected to electrospinning processes so as to form a fiber of desired cross sectional dimension and length and arranged in a desired orientation (optionally random) so as to have a resulting pore size (average distance between strands) to allow materials, analytes, active agents, etc. to pass through or be retained within or by the polymer network.

Optionally, the matrix includes 2 or more layers of polymer, optionally 3, 4, 5, 6, or more layers of polymer.

A matrix is optionally made of a hydrophilic material. Optionally, a matrix is made of a hydrophobic material. The relative hydrophobicity of the matrix may be tailored to a desired level by intermixing two or more matrix materials and/or by post-formation processing of one or more matrix materials.

In some aspects, the matrix comprises a pore size, the pore size optionally suitable for controlling sample flow or regulating the size of molecules that may pass through the system. In some aspects, the pore size within the matrix ranges from about 5 microns to about 500 micrometers (μm), or any value or range therebetween. The resulting pore size of a matrix is optionally from 10 μm to 200 μm, optionally greater than 10 μm to 40 μm, optionally 10 μm to 35 μm, optionally greater than 10 μm to 30 μm, optionally greater than 10 μm to 30 μm, optionally greater than 10 μm to 25 μm. In some aspects, the pore size of the matrix is selected to permit the flow of a liquid biological sample and any reporters or target analytes of interest present in the biological sample. In multi-layer aspects, different layers of the matrix component may comprise different pore sizes. For example, a screen layer may comprise a matrix having a pore size selected to capture and sequester cells (if desired) or other contaminants, while permitting fluid, antibodies, or other target analytes to pass through the screen layer to the membrane layer. Illustrative examples of a matrix can be found in International Patent Application Publication No.

WO 2020/086812, also teaching methods of vitrifying or incorporating molecules into a matrix.

Optionally, a matrix includes a layer of fibrous mesh, optionally non-woven. Creation of the fibrous mesh may be achieved by creation of fibers with a fiber diameter of 0.1 μm to 200 μm. Optionally, the polymer is in a fiber with a fiber diameter of greater than 0.5 μm, optionally from greater than 0.5 μm to 4 μm, optionally greater than 0.5 μm to 3 μm, optionally 0.5 μm to 2 μm.

A matrix has a thickness that is optionally 0.1 μm or greater, optionally 0.5 μm, optionally 1 μm, optionally 2 μm, optionally 5 μm, optionally 10 μm, optionally 20 μm, optionally 50 μm, optionally 100 μm, optionally 200 μm, optionally 500 μm, or greater.

In some aspects, a matrix is or includes polycaprolactone (PCL), collagen, or combinations thereof. The primary characteristics of such water stable polymers is that they are able to form networks or fibers such that one or more capture agents may be vitrified thereon or therein. Thus, the matrix must have sufficient stability in an aqueous environment so as to serve as a suitable surface for vitrification of an aqueous vitrification medium containing one or more desired molecules such as reporters and/or capture agents. Illustratively, a matrix includes PCL of or about Mn 80,000 Da.

In some aspects, the capture agent (e.g. antigen, aptamer or antibody) is covalently bound to the matrix, optionally at a test site or a control site. Alternatively, a capture agent is electrostatically bound to a matrix. Covalent bonding to a PCL water stable polymer, as an example, can be achieved by acrylating a capture agent (e.g., SARS-CoV-2 spike (S) protein or nucleocapsid (N) protein, aptamer (e.g., ACE-2 peptide or protein), or antibody (e.g. Anti-Human SARS Coronavirus Nucleoprotein Mouse MAb (40143-MM05, Sino Biologicals) or Anti-Human SARS Coronavirus Nucleoprotein Rabbit Mab (40143-R001, Sino Biologicals) by reacting the capture agent with poly(ethylene glycol) diacrylate in phosphate buffered saline including ACRL-PEG-SVA 5000, and the photoinitiator 2-hydroxy-4'-(2-hydroxyethoxy)-2-methylpropiophenone. This can then be reacted with the PCL layers by coating on one or both sides then exposing the coated layer to UV light to covalently bond the capture agent to the matrix. This results in antigen, aptamer, or antibody covalently bonded to the matrix. The resulting material can be subsequently used to vitrify one or more additional agents into the matrix or may be used in a multi-layer system with a separate layer that includes one or more agents vitrified into the matrix as described herein. Optionally, a capture agent need not be covalently bonded to a matrix or portion thereof.

Optionally, when a capture agent is an antibody, it was found that by precoating a test site (or other desired location) with an anti-Fe antibody, and subsequent localization of the capture antibody to that site improved the ability of the capture antibody to react with an analyte in a sample. Thus, a test site, control site, or other is optionally formed by first contacting the membrane with an anti-Fe antibody, dried, then contacted with a desired capture antibody at the same site. As an example, an anti-mouse IgG (Fe specific) antibody produced in goat (M4280-1ML from Sigma Aldrich), 2 mg/mL, is first striped on CN95 membrane with a dispensing rate/translating speed of 0.291 μL/mm using an Automated Lateral Flow Reagent Dispenser (ALFRD) from ClaremontBio, Upland, CA After first layer is dry, a desired monoclonal antibody (e.g. 1 mg/mL with 5% disaccharide) is coated on top of the first layer and vitrified according to the teachings of U.S. Pat. No. 10,433,540.

It was found that a capture agent could be directly vitrified during an electrospinning process to form a vitrified material layer that can be associated with or within the matrix or portion thereof. By combining pullulan, trehalose (as an exemplary vitrification agent), and a desired reporter, substrate, capture agent or combinations thereof, in an electrospinning apparatus, the pullulan will serve as a fiber forming scaffold. In this way, the capture agent, reporter, substrate or combination thereof does not crystallize during the electrospinning process, but is instead transferred into a vitrified glassy state so that the active agent can be included in a matrix or portion thereof so as to be heat and storage time stable.

A capture agent or reporter is optionally an antibody. The terms "antibody" and "antibodies" as used herein include monoclonal antibodies, polyclonal, chimeric, single chain, bispecific, simianized, and humanized antibodies, as well as Fab fragments, including the products of a Fab immunoglobulin expression library. An intact antibody, a fragment thereof (e.g., Fab or F(ab')2), or an engineered variant thereof (e.g., sFv) can also be used. Optionally, an antibody is humanized as is recognized in the art. Optionally, an antibody is not humanized. Antibodies can be of any immunoglobulin class including IgG, IgM, IgE, IgA, IgD and any subclass thereof.

A capture agent is optionally an aptamer. In aspects, a capture aptamer is or mimics (such as in the case of a nucleotide aptamer) human angiotensin converting enzyme 2 (ACE2) protein, or a peptide or fragment thereof. Human ACE2 protein is available from a variety of commercial vendors, including for example RayBiotech (Peachtree Corners, VA) and Novus Biologicals (Centennial, CO). The sequence of full length human ACE2 is available under UniProt Accession No. Q9BYF1.

The devices and methods of this disclosure are optionally suitable for detection of a wide variety of target analytes, including a diverse array of pathogens and toxins. In aspects, the capture agent comprises a nucleotide, antibody, a protein, a peptide, aptamer, or fragments thereof. In some aspects, the capture agent is a viral or bacterial nucleotide, protein, peptide, or fragment thereof. In some aspects, the capture agent is a viral antigen, including illustratively an influenza virus antigen (e.g., hemagglutinin, neuraminidase, and the like), a coronavirus antigen (e.g., a SARS-CoV protein, a SARS-CoV-2 protein, a MERS-CoV protein, and the like), an Ebola virus antigen, an HIV antigen, a poxvirus antigen, etc.; a bacterial antigen; a fungal antigen; a toxin antigen, such as a bacterial toxin or subunit thereof (e.g. anthrax); and the like.

In some exemplary aspects, the target analyte is a viral antigen(s) (optionally SARS-CoV-2 virus antigen), or host antibodies thereto (illustratively, host anti-SARS-CoV-2 IgG or IgM molecules present in the biological sample). Suitable capture agents to host antibodies to a viral antigen include, for example, SARS-CoV-2 spike (S) protein and SARS-CoV-2 nucleocapsid (N) protein. N and S proteins of SARS-CoV-2, and other viruses, are commercially available through various vendors, including for example RayBiotech (Peachtree Corners, VA). Such proteins may be full length or may include a peptide or subunit of the full length protein. For example, in aspects, the capture antigen may comprise the S1 or S2 subunit of the SARS-CoV-2 spike protein S. However, the skilled artisan will appreciate that other peptides or fragments thereof may be useful for capturing the target analyte. The SARS-CoV-2 spike protein has been characterized by Ou, et al., Characterization of spike glycoprotein of SARS-CoV-2 on virus entry and its immune cross-reactivity with SARS-CoV, Nature Communications 11, article 1620 (2020); and Ibrahim, et al., COVID-19 spike-host cell receptor GFP78 binding site prediction, J. Infect. S0163-4453(20) (Mar. 10, 2020), each of which is incorporated herein by reference in its entirety.

Optionally, a capture agent is an antibody specific for a virus, optionally the SARS-CoV-2 virus, optionally the SARS-CoV-2 virus spike protein. Illustrative examples of such antibodies include but are not limited to anti-Human SARS Coronavirus Nucleoprotein Mouse MAb (40143-MM05, Sino Biological) and anti-Human SARS Coronavirus Nucleoprotein Rabbit Mab (40143-R001, Sino Biologicals). The capture antibody may be covalently or electrostatically bound to one or more regions of the test strip such as a test region as used herein.

A reporter is optionally bound to a detectable label. Illustrative examples of a detectable label include but are not limited to an enzyme, fluorescent label, phosphorescent label, chemiluminescent label, colorimetric label, detectable particles or ligands, biotin, and the like. Examples of suitable reporter enzyme detectable labels include but are not limited to urease, alkaline phosphatase, horseradish peroxidase (HRP), glucose oxidase, and the like.

A reporter optionally is or includes an antibody. Reporter antibodies include but are not limited to anti-human antibody conjugates comprising a detectable label as the term is used herein. In some aspects, the reporter antibody includes an IgG or IgM antibody conjugated to a detectable label. Labeled reporter antibodies are available from a variety of sources, including for example Rockland Antibodies and Assays, Limerick, PA; Sigma-Aldrich, St. Louis, MO Illustratively, a labeled reporter antibody is bound to an enzyme, optionally horseradish peroxidase. Methods of bonding antibodies to horseradish peroxidase or other enzymes are known in the art and the conjugation of HRP to an antibody may be performed using the LYNX Rapid HRP Antibody Conjugation Kit available from Bio-rad antibodies, Hercules, CA.

A capture agent, reporter, substrate, or any other desired molecule may be vitrified into or onto any portion of a device according to the teachings of U.S. Pat. No. 10,433,540 and Patent Application No: PCT/US2021/019887. Briefly, a vitrification medium including one or more agents to be vitrified into a matrix are combined and placed into or onto the matrix. A vitrification medium may include at least one vitrification agent. Illustrative examples of a vitrification agent include, but are not limited to, dimethylsulfoxide, glycerol, sugars (e.g. trehalose, etc.), polyalcohols, methylamines, betines, antifreeze proteins, synthetic anti-nucleating agents, polyvinyl alcohol, cyclohexanetriols, cyclohexanediols, inorganic salts, organic salts, ionic liquids, or combinations thereof. In aspects, 1, 2, 3, 4, or more vitrification agents are included in the vitrification medium.

The vitrification agent is included in the vitrification medium at a concentration that is dependent on the identity of the vitrification agent. In some aspects, the concentration of the vitrification agent below that which would be toxic to the biological sample being vitrified. As used herein, "toxic" means that functional or biological viability is not achieved upon subsequent sample use, or the biological sample is not suitable for subsequent analyses. In various aspects, the concentration of the vitrification agent is greater than or equal to 500 micromolar ($\mu$M) and less than or equal to 6 molar (M), or any value or range therebetween. As one example, trehalose is included in various aspects in a concentration of greater than or equal to 1 millimolar (mM) and less than or equal to 6 M, optionally greater than or equal to 150 mM and less than or equal to 6 M. In some aspects, the total concentration of all vitrification agents when combined is greater than or equal to 1 mM and less than or equal to 6 M, optionally greater than or equal to 1 mM and less than or equal to 6 M.

It is contemplated that, in some aspects, the vitrification medium may further include other components, such as, by way of example and not limitation, water or other solvents, a buffering agent, one or more salts, RNase or DNAse inhibitors, or combinations thereof. A buffering agent is any agent with a pKa of 6 to 8.5 at 25° C. Illustrative examples of buffering agents include choline, betaine, HEPES, TRIS, PIPES, MOPS, among others. In some aspects, the buffering agent is a buffering agent that contains large organic ions (greater than 120 kDa), such as choline, betaine, or HEPES. In aspects including a buffering agent, the buffering agent is provided at a concentration suitable to stabilize the pH of the vitrification medium to a desired level.

Salts can include, by way of example and not limitation, sodium salts, potassium salts, chloride salts, or combinations thereof. When included in the vitrification medium, the salts can be provided at a concentration of from greater than or equal to 1 millimolar (mM) to less than or equal to 500 mM. For example, the salts may be present in a concentration of from greater than or equal to 1 mM to less than or equal to 500 mM, from greater than or equal to 1 mM to less than or equal to 400 mM, from greater than or equal to 1 mM to less than or equal to 300 mM, from greater than or equal to 1 mM to less than or equal to 250 mM, from greater than or equal to 1 mM to less than or equal to 200 mM, from greater than or equal to 1 mM to less than or equal to 150 mM, from greater than or equal to 1 mM to less than or equal to 100 mM, from greater than or equal to 1 mM to less than or equal to 75 mM, from greater than or equal to 1 mM to less than or equal to 50 mM, from greater than or equal to 1 mM to less than or equal to 25 mM, from greater than or equal to 25 mM to less than or equal to 500 mM, from greater than or equal to 25 mM to less than or equal to 400 mM, from greater than or equal to 25 mM to less than or equal to 300 mM, from greater than or equal to 25 mM to less than or equal to 250 mM, from greater than or equal to 25 mM to less than or equal to 200 mM, from greater than or equal to 25 mM to less than or equal to 150 mM, from greater than or equal to 25 mM to less than or equal to 100 mM, from greater than or equal to 25 mM to less than or equal to 75 mM, from greater than or equal to 25 mM to less than or equal to 50 mM, from greater than or equal to 50 mM to less than or equal to 500 mM, from greater than or equal to 50 mM to less than or equal to 400 mM, from greater than or equal to 50 mM to less than or equal to 300 mM, from greater than or equal to 50 mM to less than or equal to 250 mM, from greater than or equal to 50 mM to less than or equal to 200 mM, from greater than or equal to 50 mM to less than or equal to 150 mM, from greater than or equal to 50 mM to less than or equal to 100 mM, from greater than or equal to 50 mM to less than or equal to 75 mM, or any and all ranges or sub-ranges included therein.

A capture agent, reporter, substrate, or any other desired material may be vitrified into or onto a particular device, optionally according to the teachings of U.S. Pat. No. 10,433,540. Optionally, the molecule(s) to be vitrified may be combined in a vitrification solution including a sugar (e.g. trehalose) and that further includes a combination of divalent metal ions and a chelator. Illustrative examples of divalent metal ions includes salts of Ca, Mg, Co, Fe, Zn, Mn among others. Illustrative salts include chloride, sulfate, etc. Chelators include polyols, ethylenediaminetetraacetic acid (EDTA), egtazic acid (EGTA), among others. The molar ratio of divalent metal salt to the chelator in the vitrification solution may be 10:90 to 90:10, optionally 50:50.

The detection of the analyte may be performed by detection of the reporter at a test site or control site by any suitable method. Illustratively, detection includes a fluorescence reader matched to the reporter, colorimetric assay, direct detection of label on the reporter molecule (e.g. gold or other), chemiluminescence or other such assay system. In some aspects, a fluorescence reader is a light that emits a wavelength suitable to excite a detectable label such that fluoresce emission will occur for detection.

Illustratively detection of an analyte is performed using an enzyme/substrate system (e.g. horseradish peroxidase (HRP) or alkaline phosphatase (AP) coupled with a substrate such as 4-chloro-1-naphthol (4-CN), 3, 3'-diaminobenzidine (DAB), p-Nitrophenyl Phosphate (PNPP), CSPD and CDP-Star substrates, DynaLight Substrate with RapidGlow Enhancer, o-phenylenediamine dihydrochloride (OPD), 3,3', 5,5'-tetramethylbenzidine (TMB) or its derivatives (e.g. TMBM, TMBMX), 2,2'-Azinobis [3-ethylbenzothiazoline-6-sulfonic acid]-diammonium salt (ABTS), SuperSignal ELISA Pico Chemiluminescent Substrate, SuperSignal ELISA Femto Maximum Sensitivity Substrate, and the like, available from ThermoFisher Scientific (Waltham, MA) and other commercial vendors. In some aspects, a label is a fluorophore (e.g. Cy3, Cy5, alexafluor 488, alexaflour 647, or other). Illumination with an LED or other of appropriate wavelength source will allow specific detection of the presence or absence of the desired molecule of interest.

Optionally, a substrate as used in any aspect as described herein is TMB (3,3',5,5'-tetramethylbenzidine), ABTS (2,2'-Azinobis [3-ethylbenzothiazoline-6-sulfonic acid]-diammonium salt), OPD (o-phenylenediamine dihydrochloride), PNPP (p-Nitrophenyl Phosphate), ONPG (o-nitrophenyl-$\beta$-D-galactopyranoside), or any combination thereof. Such substrates are functional, illustratively, with HRP or alkaline phosphatase as an enzyme on a reporter.

In some aspects, a target analyte is detected using a reporter that is or includes an enzyme such as HRP that is reacted with a substrate that is optionally an insoluble substrate. An insoluble substrate is one that generates an insoluble product and thereby provides for more improved localization in solid phase assays such as those provided herein. An insoluble substrate as provided herein does not necessarily require that the substrate itself be insoluble in an aqueous system, but that the product generated by the action of the enzyme generates an insoluble product. Illustrative non-limiting examples of insoluble substrates include derivatives of 3,3',5,5'-tetramethylbenzidine (TMB) such as TMBM, TMBMX, and 3, 3'-diaminobenzidine (DAB) available from MOSS, Inc. Pasadena, MD.

In other aspects, a substrate may be a molecule that is specifically cleaved by a target analyte such as an enzyme. As an example, when a target analyte is an enzyme, localization of the target analyte at the test site by binding the capture agent allows for specific cleavage of the target substrate at the test site. In some illustrative examples, such a substrate may be a molecule that includes a quencher and a fluorophore such that prior to reaction with the target analyte, the fluorescence of the fluorophore is quenched. When contacted to an enzyme target analyte, the substrate is cleaved allowing the fluorophore to fluoresce. Illustrative examples of such a substrate include, but are not limited to fluorescein isothiocyanate (FITC)-labeled casein such as that found in the protease activity kit available from ABCAM (Cambridge, UK). Alternatively, a substrate is paranitrophenyl-$\alpha$-D-glucopyranoside which is converted to glucose and paranitrophenol by action of a glucosidase in the presence of hydrogen peroxide (which itself may be vitrified into the first matrix or other region in a device). The glucoside when being present in the test site following interaction with a capture agent is then active to cleave the paranitrophenyl-$\alpha$-D-glucopyranoside to generate a yellow product. The reaction may optionally be stopped by the addition of an alkaline sodium carbonate solution, if desired, but such a stopping is absolutely not necessary in the lateral flow assay devices and methods as used herein.

In alternative aspects, a substrate is localized to a test site such as by covalent or electrostatic bonding or by other binding reagent to the test site. When an enzyme is colocalized or otherwise moves across the test site, the action of the enzymatic target analyte. Should the colorimetric portion of the reaction product remain localized the resulting signal will remain localized to the test site as well leading to a robust color localization and positive readout.

A wash solution may be added to remove non-specifically bound immune complexes. Suitable wash solutions include water, buffers, or other. Optionally, the use of a wash solution is absent. In a lateral flow assay system, use of a wash solution is optionally absent.

In some aspects a reporter is bound to a detectable label in the form of a particle, such as a nanoparticle. Nanoparticles are particles with a nanoscale cross sectional dimension, e.g., from 1 nm to 1000 nm. Optionally a nanoparticle has a cross sectional dimension 1-300 nm, 5-80 nm, or 8-60 nm. Many nanoparticles are roughly spherical in shape such that the cross-sectional dimension may be considered the diameter of the spherical particle. The hydrodynamic radius or diameter can also be used to define the nanoparticle size.

A nanoparticle is optionally a metal or metalloid, latex, magnetic beads, colloidal gold, gold nanoshell particle, polystyrene, carbon, or a micelle that includes in its core a label, optionally an enzyme such as HRP. The nanoparticles may be tailored to express a carboxyl or ester of N-hydroxysuccinimide (NHS) to allow strong covalent coupling to a primary amine. Other examples of linkage options include modification of nanoparticles with maleimide and subsequent linkage to a reporter agent having an exposed thiol (generated, for example, by treating the reporter agent with mercaptoethylamine or 2-iminothiolane (Traut's reagent)); modification of nanoparticles with hydrazine and linkage to a reporter agent with oxidized glycan (aldehyde); or use of click chemistry (e.g., modification of nanoparticles with strained alkyne and linkage to a reporter agent modified with azide). In addition or alternatively, a nanoparticle may be suitable for a non-covalent interaction with a reporter agent. An example of a non-covalent linkage is a biotin-streptavidin link, where one member of the conjugate is biotinylated and the other member of the conjugate is linked to streptavidin.

In some aspects, a nanoparticle is a nanoshell particle, optionally a nanoshell particle whereby a core (optionally silicon oxide) is coated with a layer of gold. Illustrative nanoshell particles may be obtained from NanoComposix, San Diego, CA It was found that adjusting the ratio of the thickness of a shell to the radius of the core will alter the resulting color of the particles. For example, increasing the ratio of core radius to shell thickness shifts the color of the particles to the red. As such, by tailoring the ratio of the core radius to the shell thickness the color of the particles can be tuned to match or substantially match the color of the product produced by an enzymatic reaction thereby bolstering the signal found at the test site. In some aspects, it was found that the color of the nanoshell particle itself was sufficient to produce a positive signal visible to the naked eye at pg/ml amounts of analyte. The ratio of core radius to shell thickness is optionally 3:1 to 1:3, optionally 1:3 to 1:12 or any value or range therebetween.

Formation of reporter/particles may be performed using techniques recognized in the art. For example, a reporter agent may be first conjugated to a label (e.g. enzyme or other) and the labeled reporter agent then conjugated to a particle such as a gold particle or nanoshell particle. Alternatively, the particle may be first bound to the label and optionally then the label or particle bound to the reporter agent. A conjugation kit from BioRad (Hercules, CA) may be used to conjugate the label to the particle or reporter agent. A conjugation kit from NanoComposix may be used to bond the label or labeled reporter agent to the particle. If the particle is NHS bound, a conjugation kit from CytoDiagnostics may be used to bind the label and/or the labeled reporting agent to the particle.

It was found that, contrary to the understanding in the art, improved signal could be generated by coupling reporter agents to a nanoparticle whereby some of the reporter agents are bound to a label and some reporter agents were not bound to a label. For example, when a reporter antibody bound to an enzyme such as HRP is used, improved detection of the target analyte could be achieved by combining both enzyme labeled antibody along with non-enzyme labeled antibody at a particular set of ratios that resulted in both improved signal as well as reduced noise in the system. Illustratively, a ratio of the number of labeled antibodies to non-labeled antibodies is 80:20 to 20:80. Optionally, the ratio of the number of labeled antibodies to non-labeled antibodies is about 80:20:70:30, 60:40, 50:50:40:60, 30:70, or 20:80. Optionally, in some exemplary aspects, a reporter agent is an antibody that specifically binds a virus, optionally the SARS-CoV-2 virus spike protein. A particle may be coated with the antibody whereby the ratio of the number of antibodies the are also bound to a detectable label or enzyme to the number of antibodies that are not bound to a detectable label or enzyme are 80:20 to 20:80, optionally 50:50.

In some aspects, the devices described herein may further include a removable separator layer disposed between layers, channels, or regions of an assay. Optionally, the separator is removed to allow contact between analytes, reporters, and capture molecules.

In some exemplary aspects, a capture agent may be an enzyme. The enzyme capture agent is immobilized on the membrane strip at one or more target sites. When a target analyte or molecule bound to a target analyte interacts with the enzyme at the target site, enzymatic conversion of the target analyte, or molecule bound to the target analyte can generate a detectable signal indicating the presence of the target analyte at the target site. As a non-limiting example, a capture agent may be an upstream component of an enzymatic cascade whereby the capture agent converts a target analyte into a functional molecule (e.g. enzyme) itself. Using a substrate specific for the functional molecule, detection of the target analyte may be achieved at the target site.

As one illustrative aspect, a capture agent is an enzyme (e.g. glucose dehydrogenase or diaphorase). A sample may be applied to a sample pad that has a detergent (e.g. dodecyltrimethylammonium bromide (DTAB)) that will liberate the desired molecules from the biological sample. A vitrified substrate may be included in the conjugate pad of the device whereby wetting of the conjugate pad will rehydrate the vitrified material allowing the substrate to be carried to the site of action at the target site with the enzyme capture agent immobilized thereto.

In some aspects, a device or method as provided herein may utilize a competitive system for detection of the presence or absence of a target analyte. As one non-limiting example, a capture agent and target antigen may compete for the same site on target analyte (e.g. direct competitive interaction), or the binding of the target analyte to a reporter may perturb the reporter such that the reporter will no longer bind the capture agent (e.g. non-competitive inhibition). Thus, the absence of a signal at a target site alone or when combined with a positive signal at a control site, will indicate the presence of a target analyte in a sample.

In other aspects, a capture agent may be a nucleotide. A nucleotide as used herein is a sequence of nucleic acids. A capture agent may be an unlabeled nucleic acid strand with a particular sequence, or optionally a strand with a quencher. A labeled strand with a detectable labeled may be bound to the unlabeled strand at the target site. In the presence of a nucleotide with a particular sequence, the labeled strand will dissociate due to the competitive nature of the target analyte with the interaction between the labeled and unlabeled strands and the liberation of the labeled strand will produce a detectable signal indicating the presence of the target analyte.

In the devices and methods as provided herein, a biological sample may be applied to a sample pad. The sample pad may include one or more vitrified assay reagents therein. Such vitrified assay reagents may include buffers, detergents, salts, or any other needed reagent. Such description is also applicable to a sample port as otherwise described herein. As one example, a sample pad may include vitrified therein a detergent and/or a buffer whereby the rehydration of the sample pad by the liquid biological sample allows the stored assay reagents to be functional to alter one or more characteristics of the sample applied (e.g. pH adjustment, lysing one or more components, etc.).

Optionally, the target analyte is a bacteria. As one non-limiting example, detection of a bacteria may be performed by adding a biological sample to a sample pad (or sample port) that includes therein vitrified detergent (e.g. DTAB). The rehydration of the vitrified detergent allows the detergent to lyse the bacterial cells in the biological sample thereby releasing intracellular target analyte (e.g. NAD). A capture agent may be bound to a labeled target analyte (e.g. HRP or biotin labeled NAD) whereby the labeled target analyte is competitively removed by the target analyte at the target site. The reduction in color upon introduction of substrate is thereby proportional to the amount of target analyte in the biological sample.

The detection limit of the assays and methods disclosed herein is advantageously superior to traditional ELISA methods and solid phase assays. In aspects, the detection limit for the analyte of interest is less than about 1000 pg/ml, optionally less than about 100 pg/ml, optionally less than about 10 pg/ml, optionally less than about 5 pg/ml, optionally less than about 2 pg/ml, optionally less than about 1 pg/ml, optionally less than about 0.9 pg/ml, optionally less than about 0.8 pg/ml, optionally less than about 0.7 pg/ml, optionally less than about 0.50 pg/ml, optionally less than about 0.4 pg/ml, optionally less than about 0.30 pg/ml, optionally less than about 0.2 pg/ml, optionally less than about 0.1 pg/ml.

The lateral flow assays as provided herein can be completed extremely rapidly while providing the excellent low limit of detection of analyte. Detection is optionally performed in 20 minutes or less, optionally equal to or less than about 19, 18, 17, 16, 15, 14, 13, 12, 11, 10, 9, 8, 7, 6, 5, 4, 3, 2, or 1 minute(s). As such, the term "rapid" as defined herein is optionally 20 minutes or less, optionally equal to or less than about 19, 18, 17, 16, 15, 14, 13, 12, 11, 10, 9, 8, 7, 6, 5, 4, 3, 2, or 1 minute(s).

The target analyte may be quantified by one of many possible methods. Illustratively, multiple test strips are present on a matrix with different known amounts of capture antigen or aptamer or antibody allowing for quantitative determination of analyte in the sample, optionally by comparison to known controls, such as a color map. Optionally, direct quantification may be achieved by signal level in a single membrane strip or other test region in or on a matrix.

In another aspect, a kit is provided, the kit comprising any of the devices disclosed herein, reagents necessary to carry out the methods described herein, and optionally instructions for use.

Referring to FIGS. 1-4, in some aspects, a rapid diagnostic device 100a, 100b and methods of use are provided. FIG. 1 depicts an exemplary multilayered device 100a comprising a membrane layer 105 comprising a first matrix 110, having capture antigens 120 vitrified into the first matrix 110, the capture agents 120 optionally covalently or electrostatically associated with the first matrix 110. In some specific aspects, the capture antigen is a SARS-CoV-2 antigen, such as a spike or nucleocapsid protein or peptide or other. Optionally, a screen layer 155 is disposed on or otherwise in contact with the membrane layer 105, the screen layer comprising: a second matrix 160 optionally configured to substantially capture contaminants present in a liquid biological sample when the screen layer 155 is contacted with the liquid biological sample. As shown in FIG. 1, optionally at least one reporter is vitrified into the first matrix 110. In some aspects, the reporter includes or is labeled anti-human IgM 130 or labeled anti-human IgG 140.

Figure 2A:
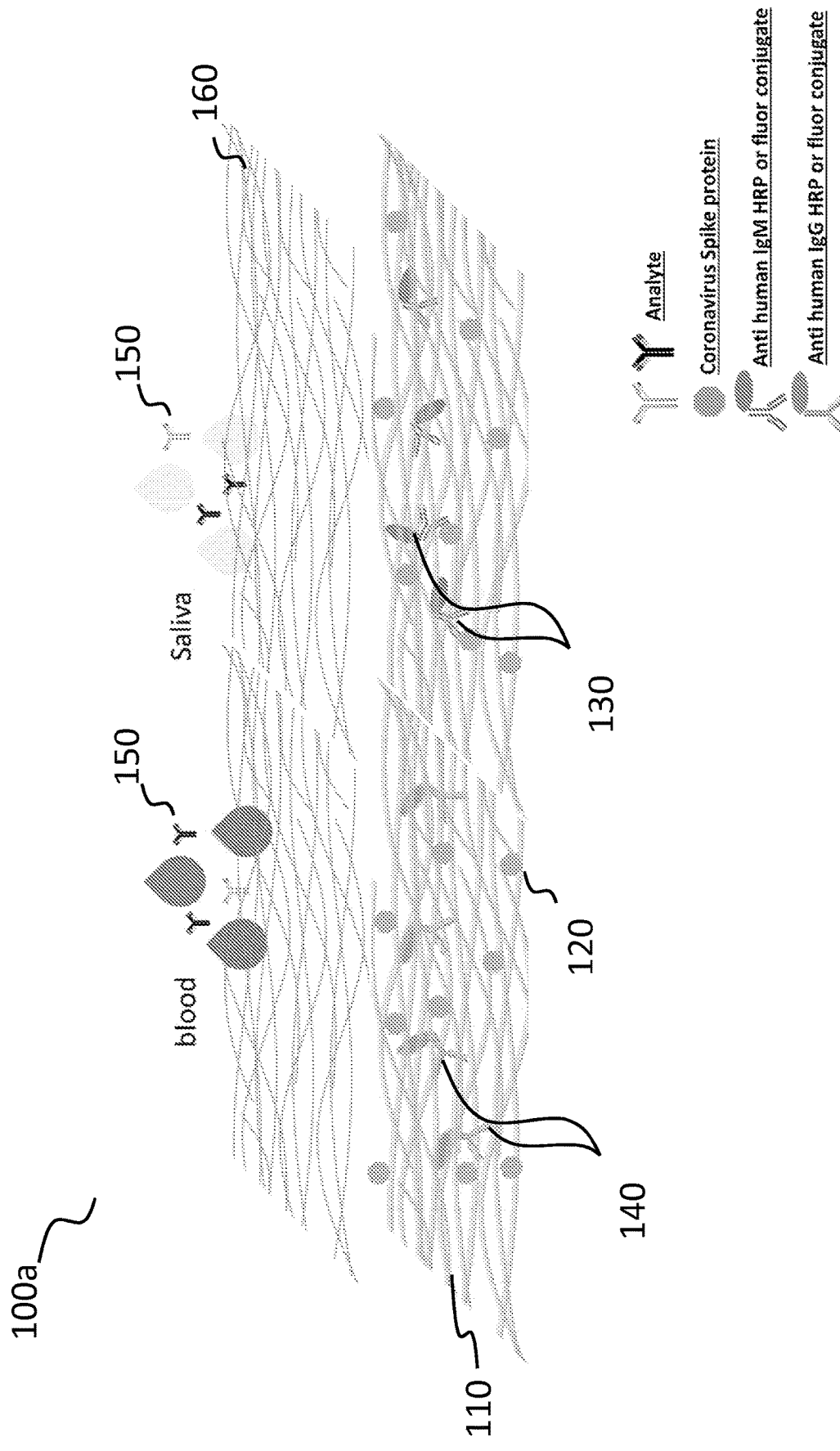
FIG. 2A illustrates a method step according to the present disclosure, wherein the device according to FIG. 1 is contacted with a liquid biological sample comprising an analyte.
Figures 2B, 2C:
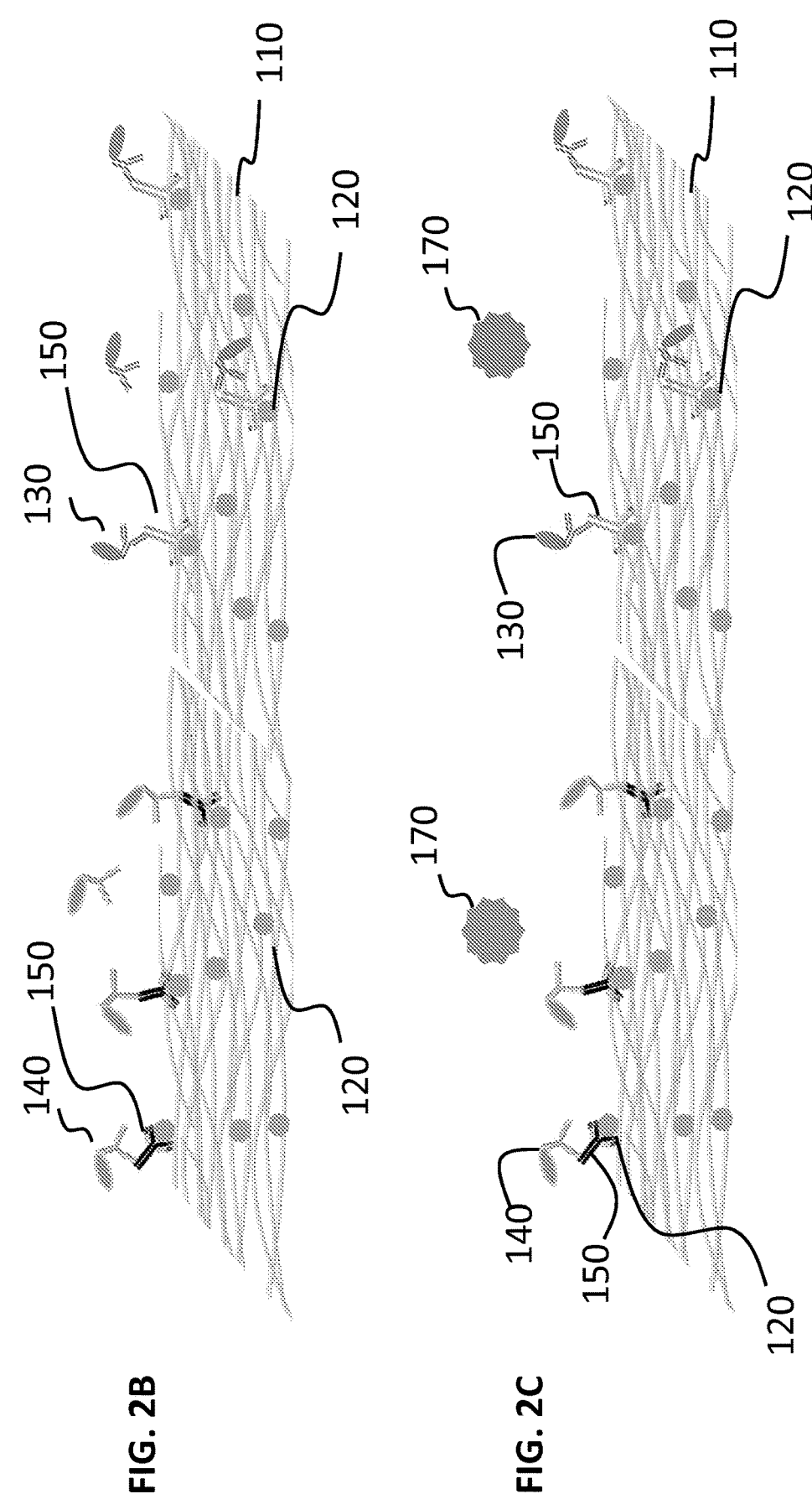
FIG. 2B illustrates a method step according to the present disclosure, wherein the target analyte binds the capture antigen and the reporter antibody in the membrane layer.
FIG. 2C illustrates a method step according to the present disclosure, wherein substrate is added to the device and a signal is detected.

FIG. 2A illustrates a step of contacting the device 100a of FIG. 1 with a liquid biological sample, illustratively blood or saliva, comprising target analytes 150. Optionally, the target analyte 150 includes human IgG and/or human IgM antibodies specific for the capture antigen 120, such as a SARS-CoV-2 capture antigen or aptamer. Referring to FIG. 2B, upon contact with a liquid biological sample, the membrane layer 105 is rehydrated and reporter antibodies 130, 140 are released from the matrix 110 and become mobile in the system, available to bind with target analyte 150. Referring to FIG. 2C, upon addition of the appropriate substrate, bound reporter antibodies 130, 140 are detected via signal 170. Optionally, strength of the signal 170 correlates with concentration of the target analyte, thereby permitting quantification of the analyte in the sample by comparing to a known standard.

Figure 3:
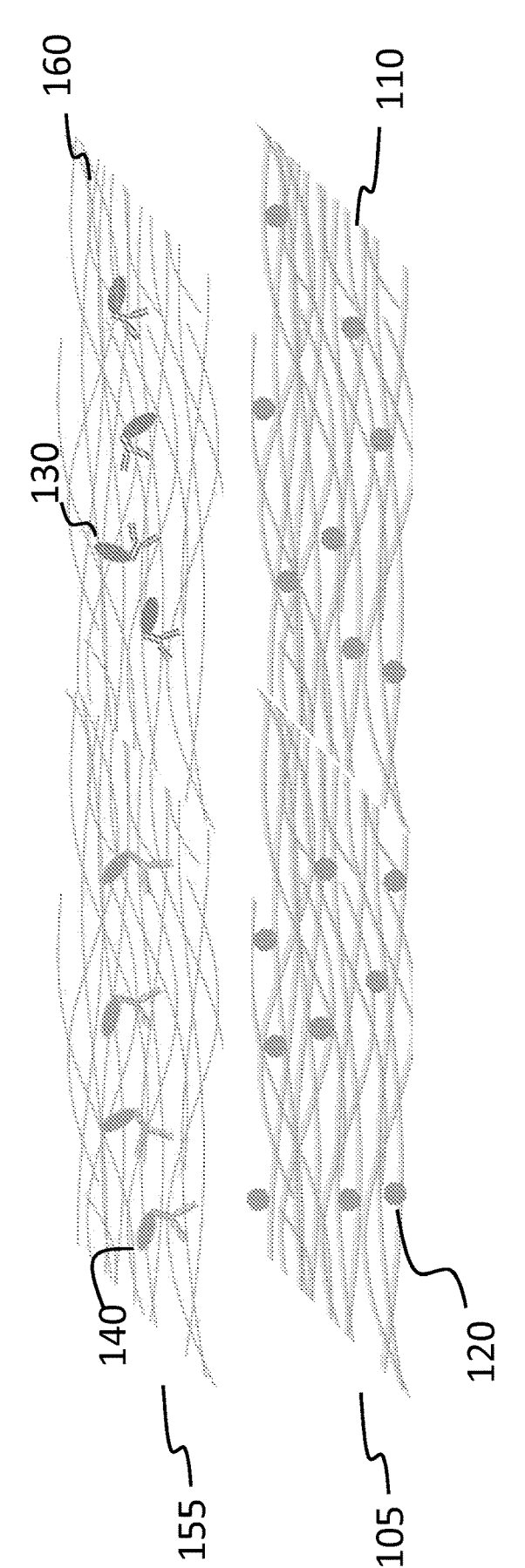
FIG. 3 illustrates an exemplary aspect of a device according to the disclosure, wherein capture antigen is vitrified in the membrane layer and reporter antibodies are incorporated into the contaminant screen layer.

FIG. 3 depicts an exemplary multilayered device 100b, comprising a membrane layer 105 comprising a first matrix 110, having capture agents in the form of antigens or aptamer 120 vitrified into the first matrix 110, the capture agents 120 optionally covalently or electrostatically associated with the first matrix 110. Optionally, the capture agent is a viral antigen, optionally SARS-CoV-2 antigen, such as a spike or nucleocapsid protein or peptide or other. A screen layer 155 is disposed on or otherwise in contact with the membrane layer 105, the screen layer includsin: a second matrix 160 optionally configured to substantially capture contaminants present in a liquid biological sample when the screen layer 155 is contacted with the liquid biological sample. At least one reporter agent (depicted as a labeled antibody for illustration) 130, 140 is vitrified into the second matrix 160. Optionally, the reporter comprises labeled anti-human IgM 130 or labeled anti-human IgG 140. While FIG. 3 is presented as an exploded view, it is understood that the screen layer 155 may optionally be disposed on or otherwise in contact with the membrane layer 105.

Figure 4:
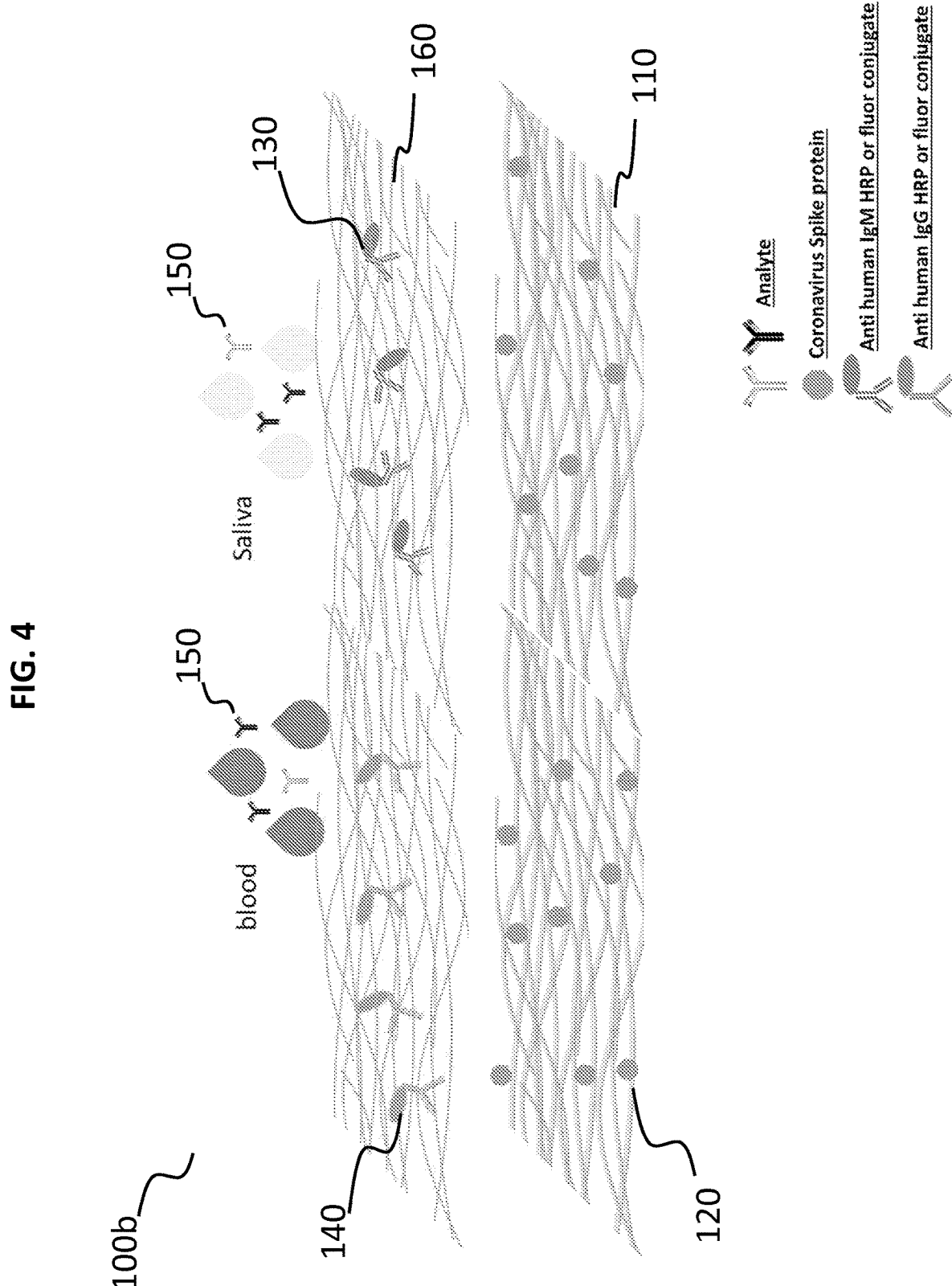
FIG. 4 illustrates a method step according to the present disclosure, wherein the device according to FIG. 3 is contacted with a liquid biological sample.

FIG. 4 illustrates a step of contacting the device 100b of FIG. 3 with a liquid biological sample, illustratively blood or saliva, comprising target analyte 150 depicted as an antibody for illustrative purposes alone. Optionally, the target analyte 150 comprises human IgG or human IgM antibodies specific for the capture antigen 120. Upon contact with the liquid biological sample, the membrane layer is rehydrated and reporters 130, 140 are released from the second matrix 160 and become mobile in the system, available to bind to target analyte. Upon addition of the appropriate substrate, bound reporter antibodies 130, 140 are detected via signal 170 as shown in FIGS. 2B-2C.

FIG. 5 illustrates an exemplary aspect of a device according to some aspects of the disclosure, wherein a removable separator layer is disposed between two channels. Channel 1 comprises a capillary channel having matrix fibers within, wherein capture molecules (illustratively, capture antibody) are covalently or electrostatically bound to the matrix fibers. Channel 2 comprises matrix fibers having reporter antibody vitrified therein, but not covalently bound. Serum is drawn into the capillary channel 1 and, when the separator is removed, channel 2 is rehydrated and the reporter antibodies are released and free to then contact the analyte of interest in the serum. The analyte of interest is captured by the capture molecule in channel 1. A magnified image of channel 1 fibers is shown at the bottom left panel. The top right panel shows fluorescent signal in channel 2 after rehydration and release of the reporter antibodies illustrating the migration thereof. The bottom right panel shows fluorescent signal in channel 1, detecting presence of the target analyte (illustratively, VEGF) by binding to the reporter.

Figure 6:
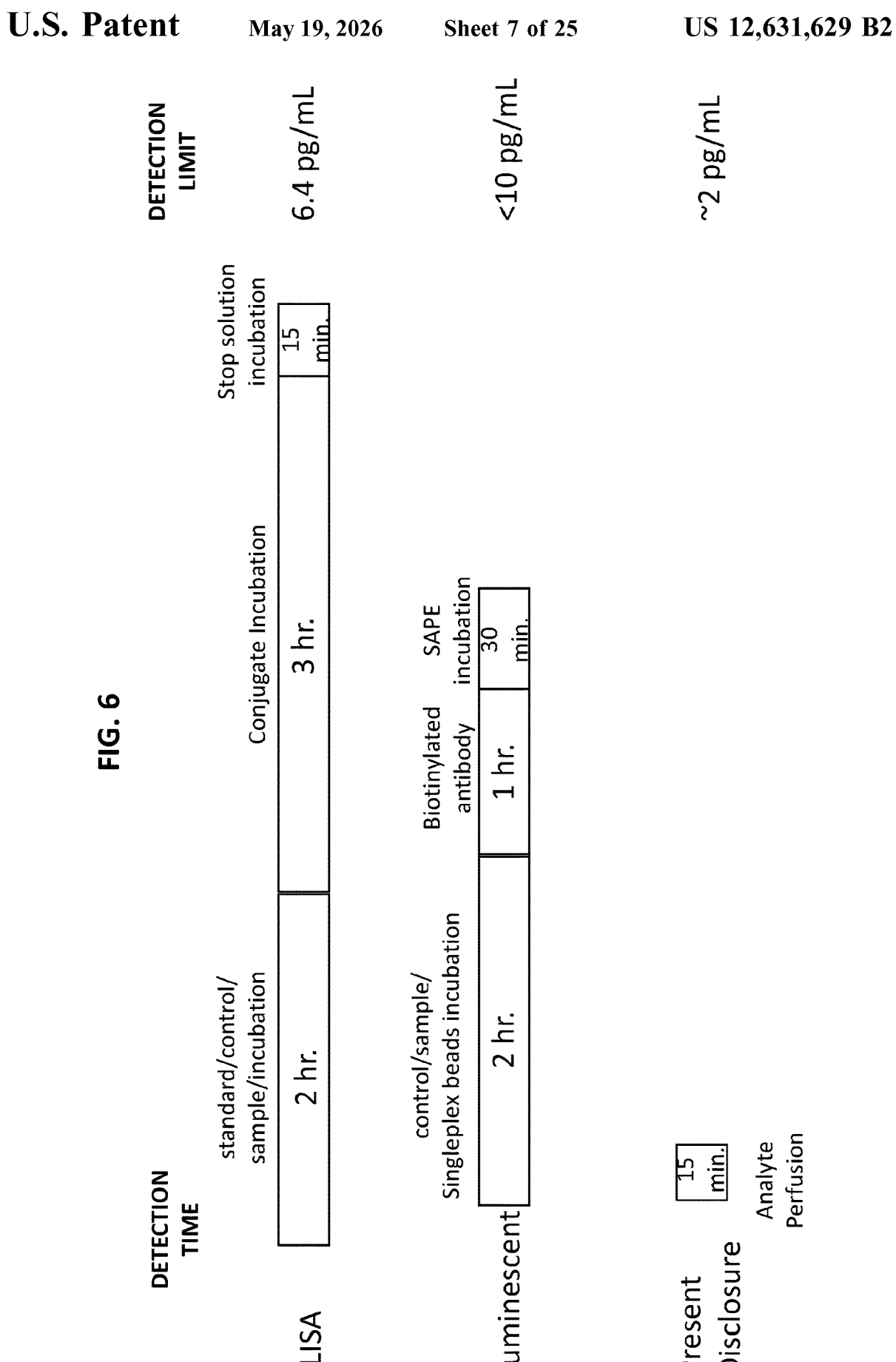
FIG. 6 illustrates exemplary comparative advantages of the presently disclosed devices and methods compared to standard available methods of ELISA and Luminex assays.

FIG. 6 illustrates the comparative advantages of the presently disclosed devices and methods compared to standard available methods. Traditional ELISA requires over 5 hours and has a detection limit of 6.4 pg/mL. Luminex® requires over 3 hours and has a detection limit of about 10 pg/mL or less. In contrast, the disclosed devices and methods permit rapid detection of target analytes at room temperature, without the need for cold-chain shipping and storage, and within about 15 minutes, at a detection limit of less than about 0.1 pg/mL.

FIGS. 7A-7C illustrate various devices in the form of an exemplary lateral flow membrane strip 200a, 200b, 200c. In the illustrated devices, the membrane strips include a conjugate pad 210, wherein labeled capture agent is vitrified therein, a test region 220, and an optional control region 230. FIG. 7A illustrates a lateral flow membrane strip 200a, wherein test and control regions 220, 230 are present as strips or lines on the membrane. FIGS. 7B and 8C illustrate lateral flow membrane strips 200b, 200c, respectively, wherein test and control regions 220, 230 are present as wells on the membrane strip. It should be appreciated that the configuration of the test and control regions may vary (i.e., strips, lines wells, circles, shapes, etc.), so long and test signals and control signals, if present, are detectable and/or discernible.

Figures 8, 9A, 9B:
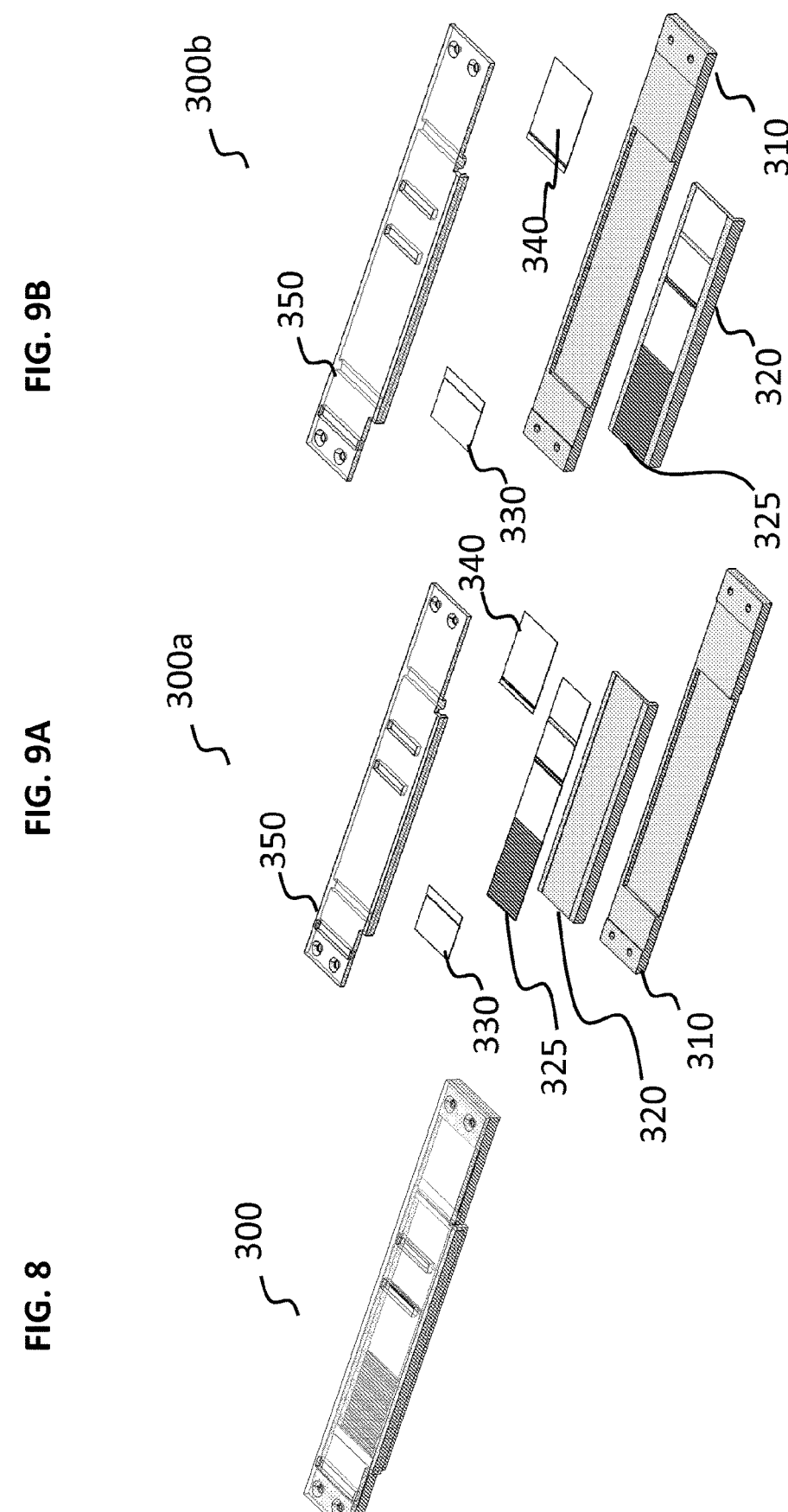
FIG. 8 illustrates an exemplary aspect of a lateral flow cassette according to the present disclosure.
FIG. 9A is an exploded view of a lateral flow cassette according to the present disclosure.
FIG. 9B is an exploded view of a lateral flow cassette according to the present disclosure.

FIG. 8 illustrates a lateral flow assay device 300 wherein a membrane is included within a housing. FIGS. 9A, 9B illustrate exploded views of housing cassettes 300a, 300b, each having a base 310, a tray 320, a membrane strip 325, a sample pad 330, a waste pad 340, and a cover 350. In FIG. 9A, the membrane strip formed to include vitrified material prior to insertion in the tray 320 of the cassette. Membrane strips are optionally removable and replaceable within the housing. In FIG. 9B, the membrane strip is vitrified on the tray 320 of the cassette, prior to assembly of the cassette. Optionally, the tray comprising the membrane strip is removable and replaceable. Optionally, the cover comprises slots or apertures for viewing control and test signals in the underlying membrane strip.

Figure 10:
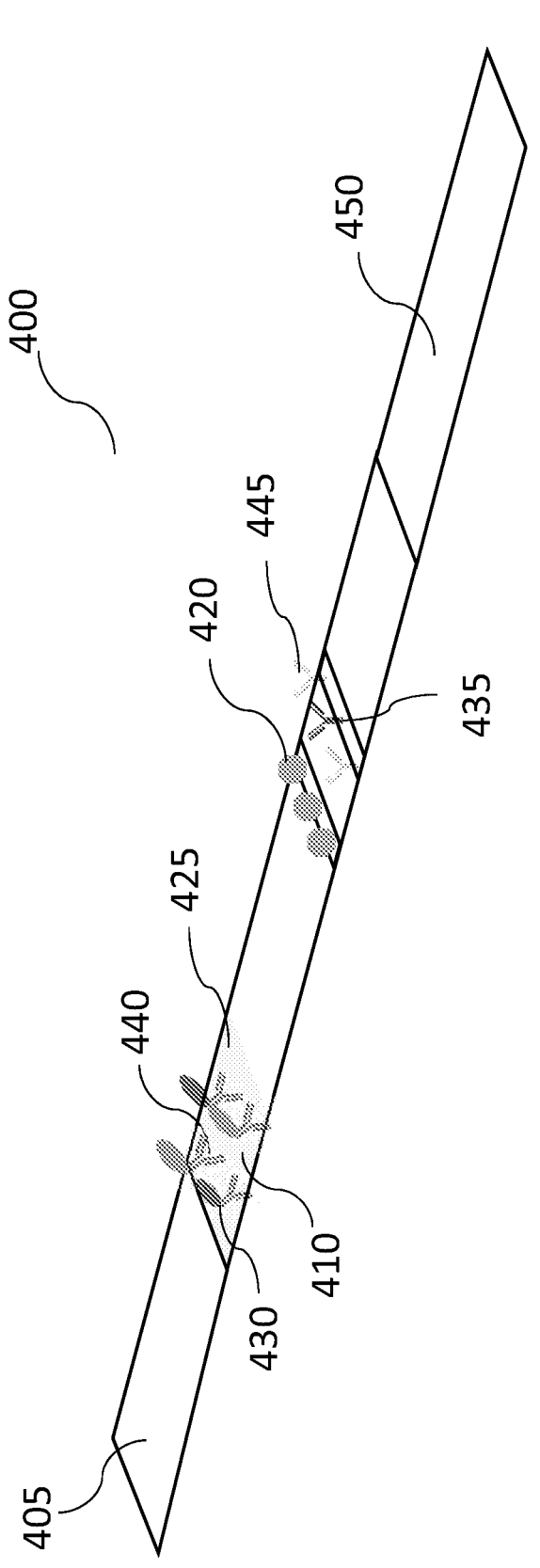
FIG. 10 illustrates an exemplary aspect of a lateral flow membrane strip according to the present disclosure.

Referring to FIG. 10, an exemplary aspect of a lateral flow membrane strip 400 is provided. The membrane strip 400 may include a sample pad 405 for receiving a liquid biological sample. The sample pad is in fluidic contact with the conjugate pad 410 comprising vitrified matrix 425. Reporter agents (optionally antibodies) 430, 440 are optionally vitrified into the matrix 425 of the conjugate pad. It is appreciated that the reporter agents may be bound to a particle as described herein. In some aspects, the device does not include reporter agents vitrified into or onto the conjugate pad, but they may be added with the sample, following the sample, or prior to contacting the sample to the sample pad. Downstream of the conjugate pad, the exemplary membrane strip includes a test site, or line, including vitrified, immobilized capture agent (e.g. antibody, antigen or aptamer) 420, optionally covalently or electrostatically bound thereto and vitrified therein or on. An optional control site, or line, may be disposed downstream of the test region, including vitrified, immobilized capture agents (e.g. antigen, aptamer or antibody) 435, 445 (illustratively, human IgG or IgM). A waste pad or absorption pad 450 may be disposed at the downstream end of the membrane strip to collect excess reagents and/or promote movement of reagents through the lateral flow assay.

Figures 11A, 11B:
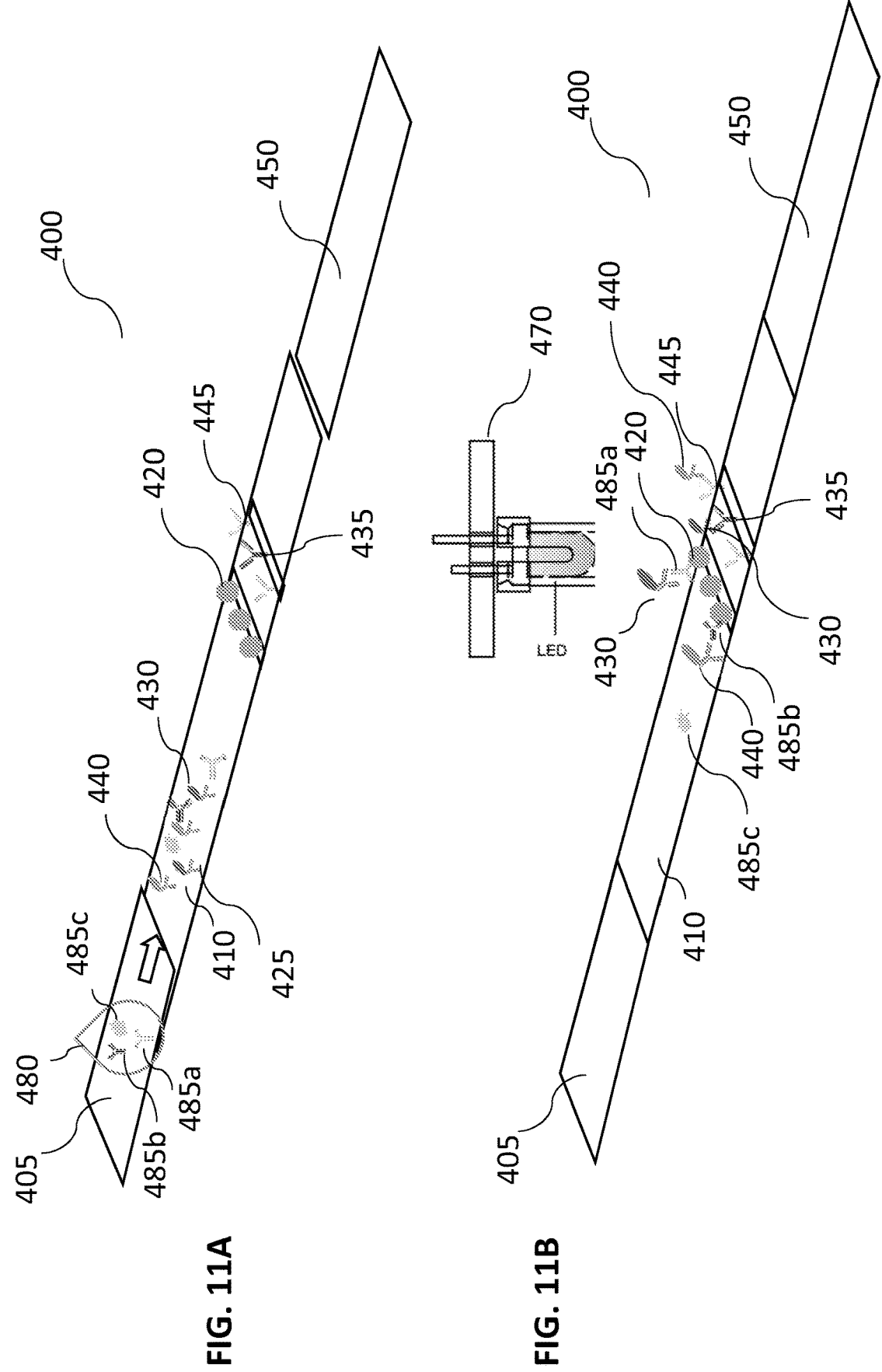
FIG. 11A illustrates a method step according to the present disclosure, wherein the lateral flow membrane strip according to FIG. 10 is contacted with a liquid biological sample.
FIG. 11B illustrates a method step according to the present disclosure, wherein the analytes of interest and unbound reporter antibodies are captured and detected on the lateral flow test strip.

FIG. 11A illustrates a step of contacting the membrane strip 400 with a liquid biological sample 480 comprising analytes of interest 485a, 485b, 485c. When the liquid biological sample 480 moistens the sample pad 405, fluid and analytes within the liquid sample move through the membrane strip by capillary action to the vitrified matrix 425. The liquid fraction of the biological sample reconstitutes the vitrified matrix 425, releasing reporter agents 430, 440, which become mobile in the system. As shown in FIG. 11B, target analytes 485 are captured by capture agent 420 at the test line. Reporter antibodies 430, 440 bind to target analyte and/or capture antibodies 435, 445 of the control line. Excess reagents are absorbed by the waste pad 450. Upon localization of the reporter and optionally further when substrate is added, signal is optionally detectable using light source 470, or by visual inspection for color change, or other means for detecting the signal.

Figures 12, 13A, 13B:
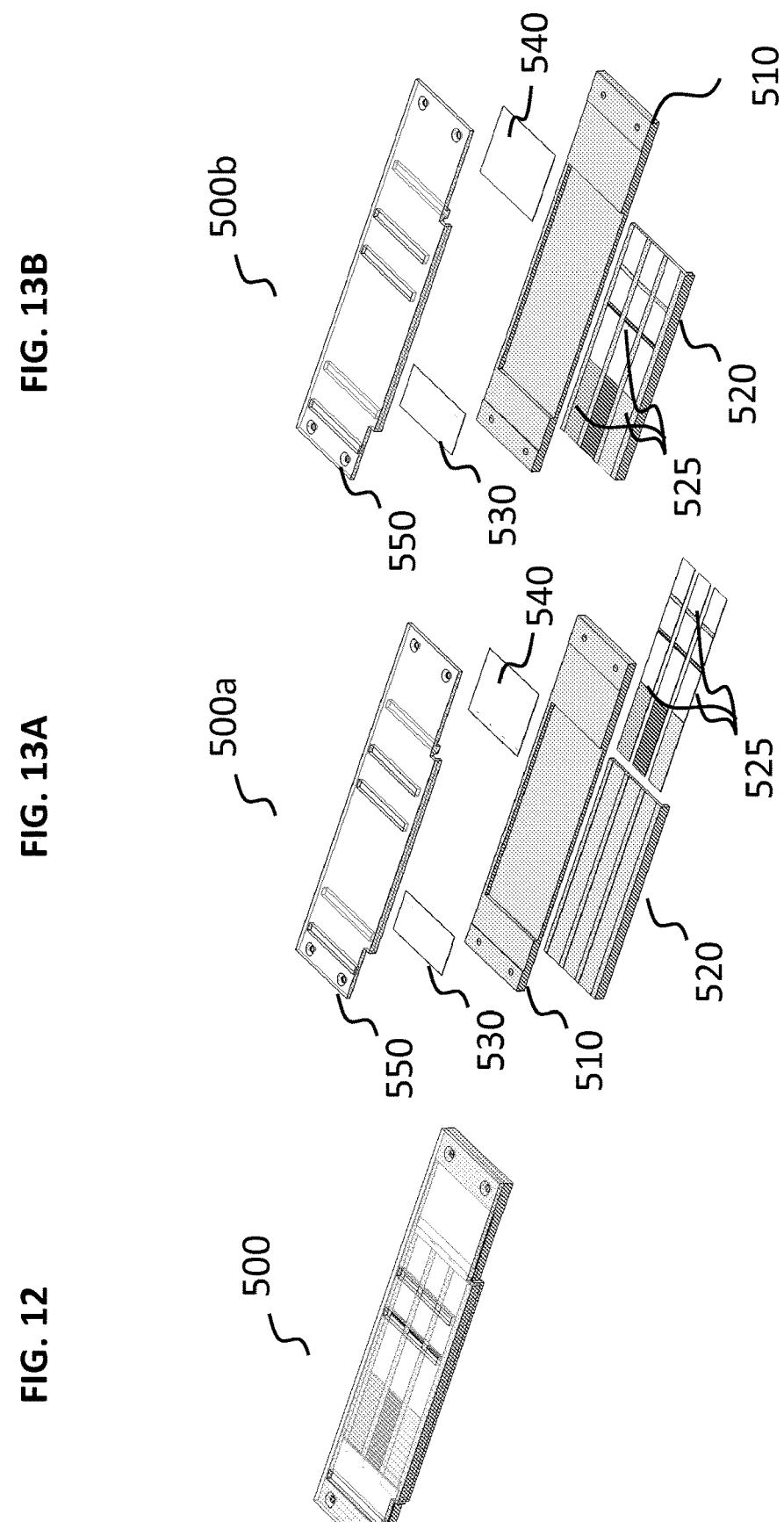
FIG. 12 illustrates an exemplary aspect of a cassette according to the present disclosure comprising a plurality of lateral flow membrane strips.
FIG. 13A is an exploded view of an exemplary aspect of a cassette according to the present disclosure comprising a plurality of lateral flow membrane strips.
FIG. 13B is an exploded view of an exemplary aspect of a cassette according to the present disclosure comprising a plurality of lateral flow membrane strips.

FIG. 12 illustrates a lateral flow assay housing cassette 500 comprising a plurality of membrane strips. FIGS. 13A, 13B illustrate exploded views of cassettes 500a, 500b, respectively, each having a base 510, a tray 520, a plurality of membrane strips 525, a sample pad 530, waste pad 540, and a cover 550. In FIG. 13A, the membrane strip is vitrified prior to insertion in the tray 520 of the cassette. Membrane strips are optionally independently removable and replaceable. In FIG. 13B, the membrane strip is vitrified on the tray 520 of the cassette, prior to assembly of the cassette. The tray 520 is optionally removable and replaceable. While test and control lines are exemplified on the membrane strips 525, it should be appreciated that the test and control regions may be in the form of lines, wells, or any other configuration permitting ready detection of signal. Optionally, the cover comprises slots or apertures for viewing control and test signals in the underlying membrane strip.

Figure 14:
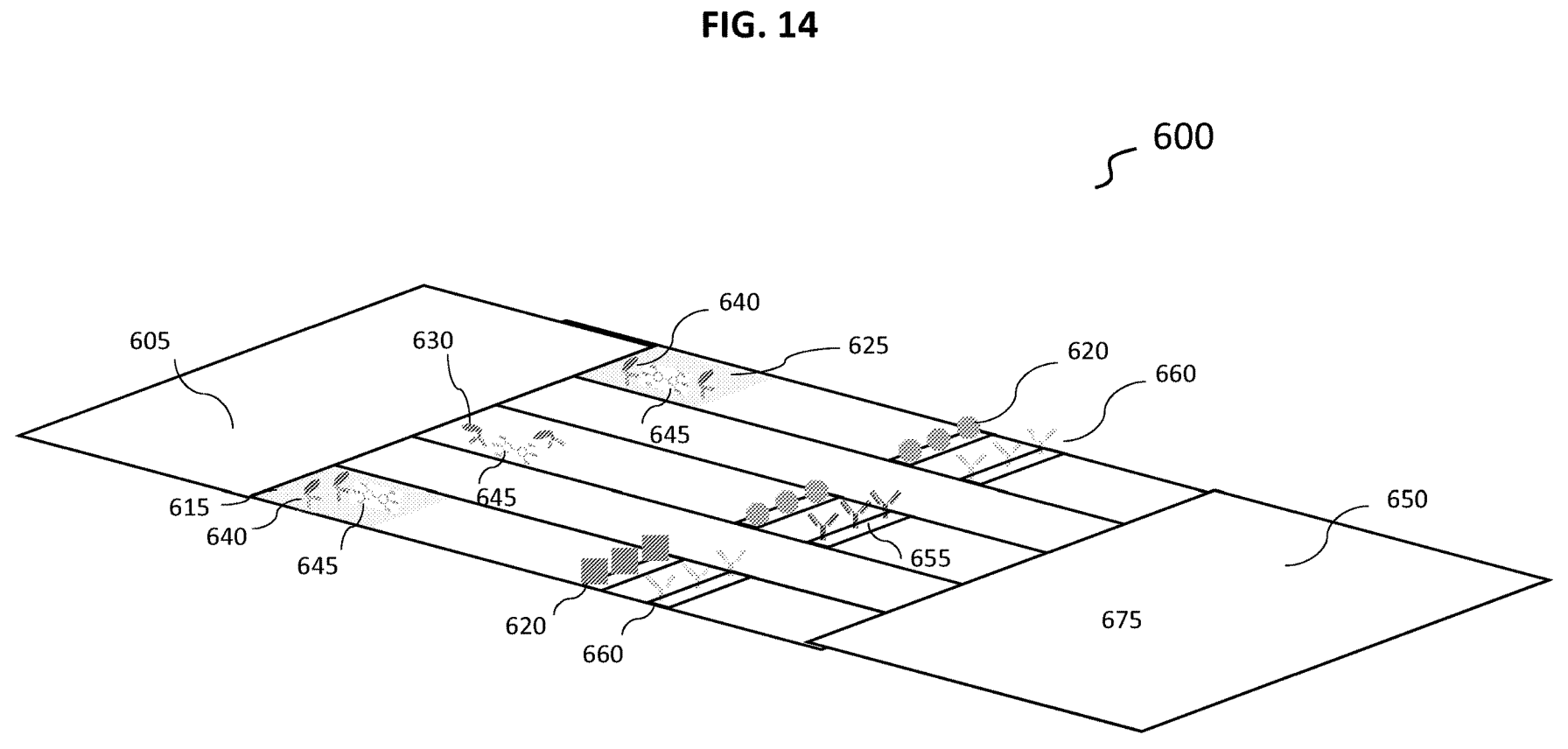
Figures 15A, 15B:
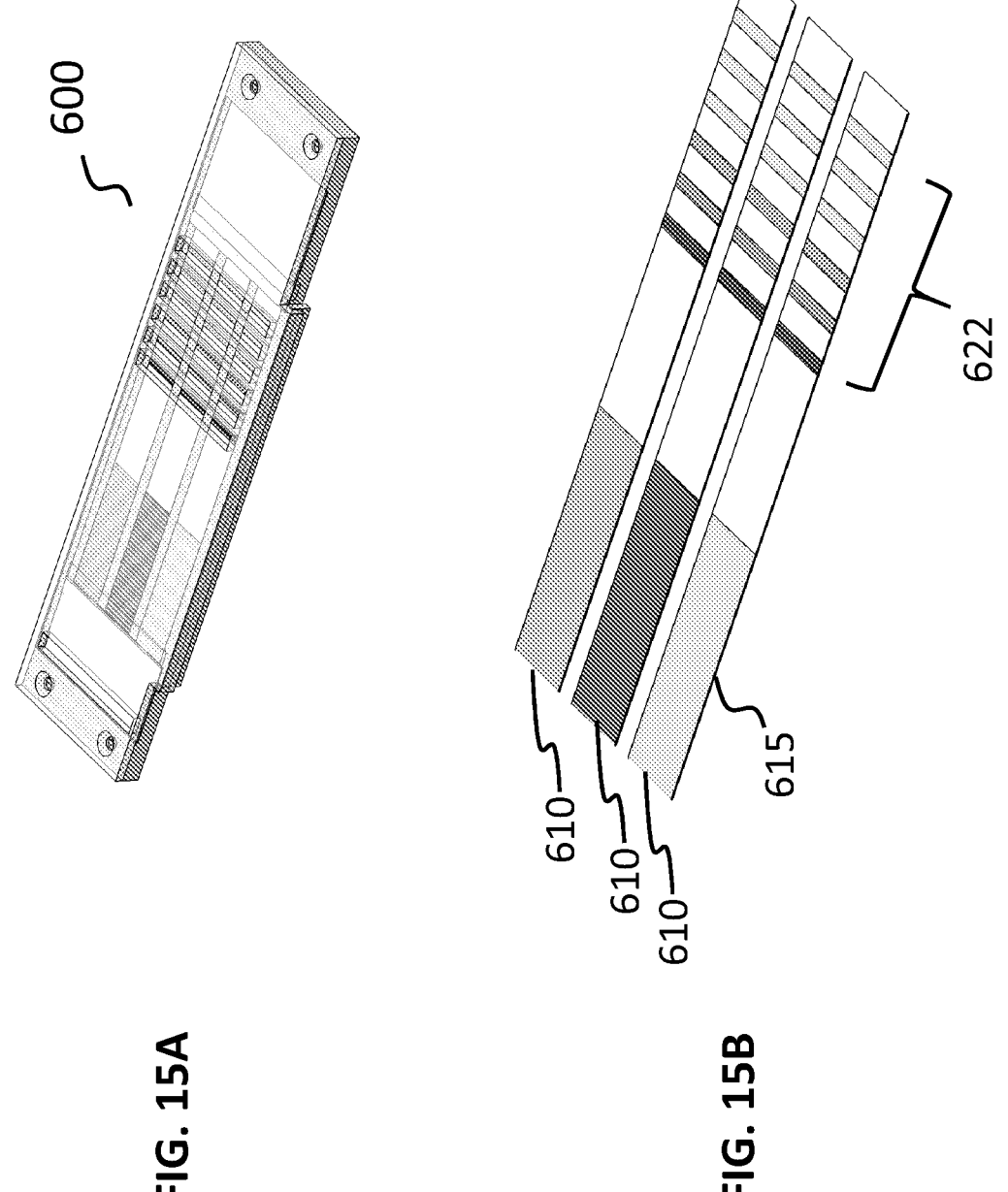
FIG. 15A depicts a lateral flow cassette having a plurality of membrane strips according to the present disclosure, each strip providing for serial dilution of the captured target analyte, for determining concentration of the target analyte.
FIG. 15B depicts a plurality of membrane strips of the cassette according to FIG. 15A.

FIG. 14 and FIG. 15 illustrate an exemplary multi-strip lateral flow assay 600 according to some aspects of this disclosure both within a housing (15A) or without a housing (15B). The assay includes a sample pad 605 for receiving the liquid biological sample. While three membrane strips are illustrated, it will be appreciated that any number of membrane strips may be included in a multi-strip assay, including 2, 3, 4, 5, or more membrane strips. Each membrane strip has a conjugate pad 615 comprising vitrified matrix, one or more vitrified reporters 630, 640, and optionally one or more substrates 645. Test lines having capture agents 620 (optionally covalently or electrostatically bound) are disposed downstream of the conjugate pad 615. Optionally, the individual membrane strips may include the same or a distinct capture agents 620. A control strip is disposed downstream of the test strip, including one or more covalently or electrostatically bound control capture agents 655, 660. A waste pad 650 is disposed downstream of the membrane strips, for receiving excess sample fluid. Optionally, the waste pad includes an indicator 675, such as a dye, that provides a color change in the presence of protein, liquid, or other indicator to indicate test completion. Illustratively, the dye includes Coomassie G-250.

When the multi-strip lateral flow assay 600 is contacted with one or more liquid biological samples, the liquid fraction of the sample moistens the sample pad 605 and flows downstream to the membrane strips. When the sample fluid reconstitutes the conjugate pad 615, the vitrified one or more reporters 630, 640 and substrates 645 are released from the matrix of the conjugate pads 615. The reporters are then free to bind target analytes in the sample. The fluid and mobile components move downstream, where "sandwich" binding is detectable at the test lines and control lines. Stop solution may be added to the sample pad to stop the reporter/substrate interaction.

Optionally, in any of the embodiments disclosed herein, a control region (e.g., strip or well) may comprise an indicator dye, such as Coomassie G-250, in addition to or in place of a capture agent. In such aspects, the indicator dye detects presence of any proteins in the liquid sample, thereby indicating completion of the test via signal, e.g., color change.

Optionally, the capture agent is an aptamer, such as an aptamer that binds an intact pathogen. Optionally, the aptamer is an ACE2 protein or peptide capable of binding viral surface proteins, optionally SARS-CoV-2 surface proteins. In some aspects, the membrane may include vitrified matrix and vitrified chromogenic agent that complexes with bound virion/aptamer complex. For example, when a liquid biological sample contacts the matrix, the matrix is reconstituted and the chromogenic agent is released. Target virions bind the capture aptamer, the chromogenic agent binds the complex, and a detection signal is produced.

Optionally, the vitrified capture agent is a biotin-labeled aptamer that binds an intact pathogen. In aspects, the membrane may include vitrified matrix, vitrified reporter, and vitrified biotin-labeled aptamer. The biotin-labeled aptamer binds virion (or other target) and the complex is captured at the test region by covalently bound avidin or streptavidin. Reporter binds the complex and a detection signal is produced.

Optionally, the vitrified capture agent is an oligonucleotide (e.g. aptamer) that binds an intact pathogen, optionally a virus, optionally SARS-CoV-2. The membrane may include vitrified matrix and vitrified beacon aptamer, the beacon aptamer having a fluorophore and a quencher. When the beacon aptamer is not bound to a target analyte, the fluorophore is quenched by the quencher and no signal is produced. However, when the beacon aptamer binds SARS-virion, the complex is captured at the test region by the covalently or electrostatically bound oligo. Signal is produced when the fluorophore of the beacon aptamer is unquenched due to aptamer-complex formation.

Optionally, the vitrified capture agent is an antibody that binds an intact pathogen, such as a virus or portion thereof such as the SARS-CoV-2 S or N protein as one illustrative example. The membrane may include vitrified matrix and vitrified capture antibody. When the liquid sample reconstitutes the capture antibody, it is free to bind any analyte within the system. In some aspects, where a reporter agent is also bound to the analyte the reporter is concentrated at the region where the capture agent is localized, optionally covalently or electrostatically localized. Detection of the presence or absence of the analyte may be achieved by color change or concentration, optionally due to a reaction with an enzyme bound to the reporter agent with a suitable substrate to generate a detectable product.

FIG. 16A depicts an exemplary diagnostic assay device 600, optionally comprising a plurality of membrane strips 610 within a housing. As shown in FIGS. 16A and 16B, each membrane strip 610 includes a conjugate pad 615 having a reporter vitrified into a matrix, and a plurality of test regions 622 including vitrified covalently or electrostatically bound capture agent for capturing target analyte. As target analyte moves downstream from the conjugate pad, capture concentration is serially diluted across the plurality of test regions 622, thereby providing a plurality of signals that may be compared to a color map or other reference standard to determine concentration of the target analyte.

Figure 16:
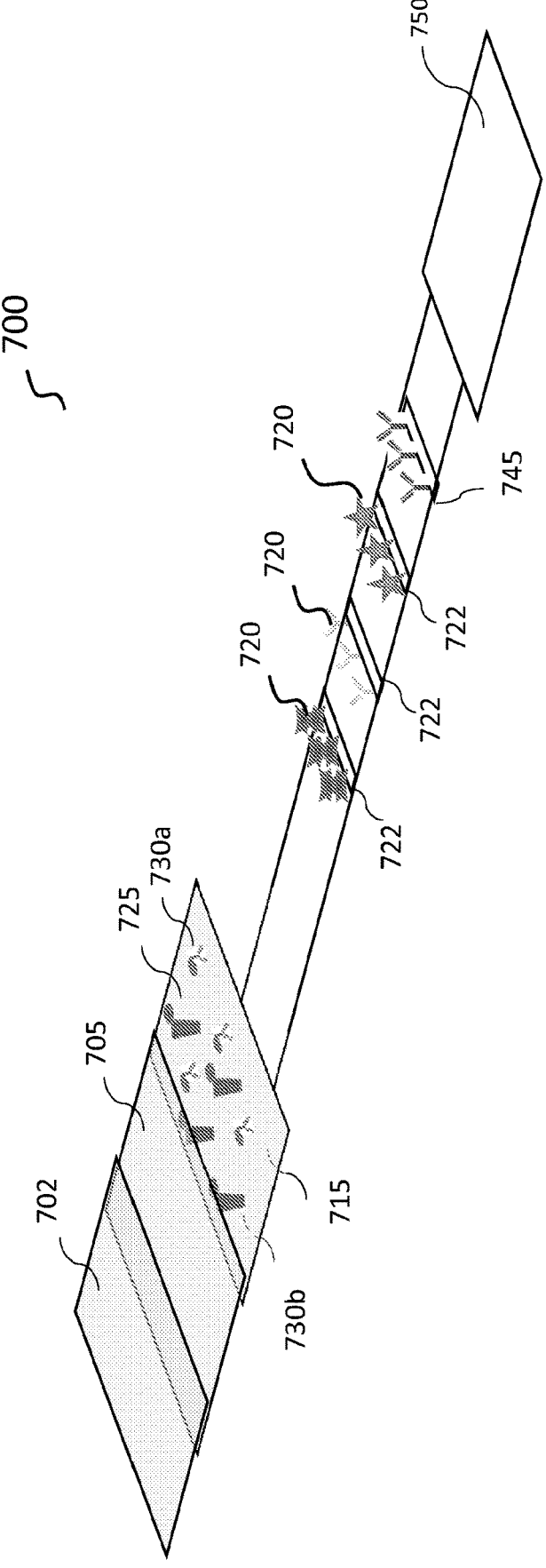
FIG. 16 depicts an exemplary membrane strip according to some aspects of this disclosure, having a plurality of test regions on a single strip.

FIG. 16 depicts an exemplary diagnostic assay device 700. Assay device 700 optionally includes a sample pad 705 and, optionally, a substrate pad 702 disposed next to and/or overlapping with and/or in contact with the sample pad 705. Optionally, the sample pad receives a liquid biological sample, illustratively a blood sample or saliva sample, and may sequester, eliminate, or destroy red blood cells in the sample (if present), such that the remaining components of the sample and target analytes may flow to the conjugate pad 715. Conjugate pad 715 includes a matrix 725 and at least one reporter 730a, 730b optionally vitrified into the matrix, and optionally bound to a particle. Optionally, the conjugate pad 715 includes at least one labeled reporter, optionally an antigen 730b vitrified into the matrix. Optionally, the conjugate pad 715 includes at least one labeled control antibody 730a vitrified into the matrix. Downstream of the conjugate pad 715 and fluidically connected thereto, optionally integral therewith, is a membrane strip including one or a plurality of test regions 722, each test region comprising a vitrified immobilized capture agent 720, the capture agent specific for the type of test analyte (e.g. human IgG, SARS-CoV-2 S protein, etc.) or specific for a control. Optionally, each test region may include a different vitrified capture agent 720, such as a capture antigen, antibody, aptamer, or the like. A control region 745 is optionally disposed on the membrane strip, optionally downstream of the test regions. In some aspects, the assay further includes a waste pad 750 for absorbing excess fluid from the sample.

In some aspects, the substrate pad 702 includes an embedded or vitrified substrate that binds a reactant suitable to development of color upon reacting with a label or labeling molecule. As a non-limiting example, a capture agent may be bound to HRP. The substrate pad may include one or more substrates for HRP (or other enzymatic label) such that when the substrate is contacted to the HRP, and at the location of the HRP on the membrane strip, a color will be produced indicating a positive result. Optionally, when the biological sample is added to the sample pad, buffer may be added to the substrate pad to reconstitute and release the substrate, such that the substrate may flow through the membrane strip to bind the appropriate reporter molecule.

In some aspects, the sample pad 705 may further include an agent that sequesters and/or lyses red blood cells, thereby permitting plasma and target analytes to move across the membrane strip. Various red blood cell lysis agents are known in the art. Exemplary agents include, but are not limited to, Red Blood Cell Lysis Buffer (available from various vendors); or an embedded solution including one or more of ammonium chloride, potassium bicarbonate, and disodium EDTA. The skilled artisan will appreciate that red blood cell lysis agents are well known in the art.

When the device 700 is contacted with a biological sample, illustratively a blood sample, comprising a target analyte, illustratively antibodies to an infectious agent, a virus itself or a portion thereof such as a viral S protein, the blood is deposited onto the sample pad. Optionally, buffer is added to the substrate pad to release the substrate molecules. Optionally, the sample pad may include an agent that sequesters and/or lyses red blood cells in the sample, thereby permitting plasma and target analytes to move across the membrane strip.

Vitrified reporters, such as labeled viral antigens 730b, and vitrified control antibody 730a are released from the conjugate pad 715 when liquid from the biological sample reconstitutes the matrix. Sample, analytes, reporter molecules, and control molecules flow downstream toward the test regions. At the test regions, discrete target analytes are captured at the desired locations according to the identity of the capture molecule at each test region. Control antibody binds the control region capture antibody to confirm the test has been completed and/or successful. In some aspects, a buffer may be added to the substrate, optionally further comprising a detecting substrate for producing a signal in the presence of "sandwich" complexes in the test regions.

Optionally, a biological sample is collected from a subject and combined with an assay buffer suitable to adjust one or more characteristics of the biological sample, and/or to liberate one or more analytes within the biological sample. As an illustrative aspect, a test sample may be saliva. The saliva may be combined with an assay buffer including a detergent to liberate the desired protein or nucleic acid analytes from the target viral system. The resulting sample may then be applied to the sample pad of a device whereby the fluid optionally reconstitutes reporter agents at the sample pad location or downstream thereof (e.g. in the conjugate pad) so that the reporter agents may be free to bind the analyte of interest within the sample. The lateral flow of the sample moves toward a test region 722 that may include one or more capture agents that also specifically bind the analyte of interest thereby capturing and localizing the analyte and reporter agent to the test site. Optionally, a substrate is applied to the test site or upstream thereof for generation of a colored product of a reaction catalyzed by an enzyme bound to the reporter agent for detection of the analyte within the sample.

In some aspects, a sample is contacted with a detergent prior to or with contacting the agent to the sample pad. A detergent is any detergent suitable for liberating a protein from a viral particle. In some aspects, an illustrative detergent is Zwittergent 3-14 (CAS 14933-09-6) optionally at 1-5% by weight in a fluid. Optionally, the detergent is combined with dithiothreitol (DTT) that may assist in improving signal results in the assay system.

Alternatively, a sample may be lysed to liberate one or more analytes on the sample pad. Optionally, the sample pad includes a detergent optionally combined with DTT, DTAB, or other detergent vitrified on the sample pad such that direct application of the sample to the sample pad reconstitutes the detergent allowing for direct liberation of the analyte from any needed source included in the sample.

Simultaneous or following the liberation of a target analyte, the sample is contacted with a reporter agent. The reporter agent may be in the same solution with the detergent, may be in a separate solution that is then combined with the sample, or the reporter agent may be housed in or on the conjugate pad in vitrified form. The reporter agent, optionally an antibody, and optionally bound to a particle, is then free to contact the analyte in the sample. Following sample movement through the conjugate pad, the capture agent at the test site concentrates and collects the analyte to the test site thereby concentrating the label on the reporter agent thereby providing for detectable signal at the test site.

It was found that in some aspects, delivery of a substrate to a target site for enhancement or development of a positive indication of the presence of a target analyte could be improved by altering the flow characteristics of the substrate through a device. It is typical for readouts in a lateral flow assay device to be performed by eye, which is less sensitive than machine readouts. This tends to push upward the limit of detection for devices when used in the field or outside of a laboratory with readout equipment suitable for sensitive color, fluorescent, luminescent or other sensitive detection. Enzymatic amplification such as the use of an enzyme bound reporter (e.g. HRP or other), boosts sensitivity, but leads to other issues to effectively localize signal generation to the desired target site.

Figure 17:
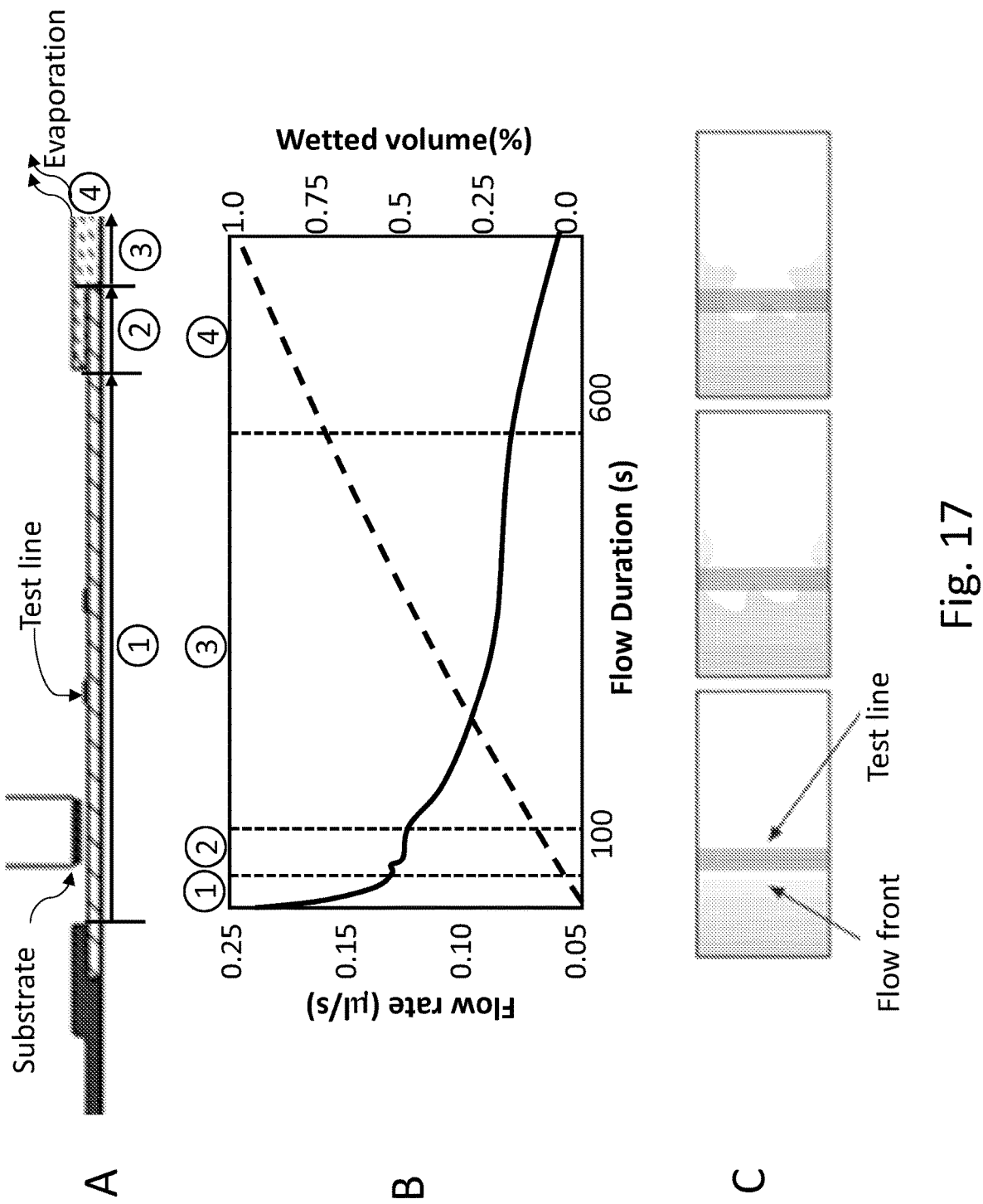
FIG. 17 illustrates an exemplary test strip according to some aspects as provided wherein: wherein A illustrates various regions of an exemplary membrane strip; B illustrates exemplary fluid flow rates and total flowed volume thoroughout the membrane strip; and C illustrates a desired linear front line following application of a substrate to the device.

It was found that the rate at which fluid (i.e. liquid biological sample or portion thereof) flows though the membrane can influence assay performance. Reduced fluid flow rates can improve the interaction between capture agent and target analyte, but may also increase the probability of the reporter being retained at a location other than the target site. This is particularly problematic when using gold or other nanoparticles as the visual agent in a reporter. When using enzymatic/fluorescent/luminescent amplification, the retention of reporters to sites other than the target site can lead to high background and/or false negatives due to nonspecific retention of the reporter which is later amplified by substrate addition. When using a lateral flow device substantially as described herein, optionally as depicted in FIG. 17A, that includes a conjugate pad and/or substrate pad that is associated with a membrane strip, the flow rate of the liquid is altered depending on the amount of liquid sample placed in the system relative to strip total volume and the time from liquid application. As illustrated in FIG. 17B, the dotted line refers to the total strip wet volume. As the flow duration proceeds to total volume the strip houses increases. As illustrated by the solid line, however, the rate at which the liquid volume flows through the membrane strip changes over time depending on the time from sample application. This can be described by breaking the overall flow rate down into four different flow regimes segmented by the vertical dashed lines in FIG. 17B. Regime 1 illustrates the initial wet out of the membrane strip. Regime 2 illustrates the wetting of the membrane strip, waste pad interface. Regime 3 illustrates the wet-out of the waste pad. Finally, regime 4 illustrates the rate due to evaporation from the waste pad (if any). Maximum flow rate is reaches in regime 1 representing the initial wet out of the membrane strip material filling the pores and moving fluid through the membrane from the conjugate pad. When the membrane strip is saturated with about 75% by volume with fluid, the flow rate substantially false. In the devices as provided herein, the channel length and width may be adjusted to improve the fluid flow characteristics and improve specific binding of the target analyte to the test site while moving unbound reporters away from the site to reduce background and improve sensitivity. A substrate may be added or a reading taken optionally at the end of regime 3, illustrated at about 8-10 min in FIG. 17B.

As such, it was found that by creating a surface flow of the substrate specifically, localization of the enzyme/substrate reaction could be more effectively localized to the target site thereby reducing the lower limit of detection, reducing false negatives, and improving signal to noise ratio. Substrate addition for enzymatic amplification poses additional challenges. The addition of liquid substrates alters the flow characteristics of the overall liquid on the membrane strip. The use of liquid substrates, therefore, overlaid the membrane strip, which is particularly true after regime 3 (the optimum time for substrate addition). If a liquid substrate is used the additional liquid pool will take a significant time to clear up the test line region and can leave non-specific signal leading to false positives.

These issues can be solved, according to some aspects as provided herein, when a substrate in dry form is optionally contacted to a membrane layer after the membrane layer is wetted with biological sample, or other. The flow of the substrate on/in the membrane layer is thereby a surface flow with a reduced amount of flow through the membrane itself. As such, according to some aspects, a substrate is vitrified into a substantially dry substrate membrane, and the substantially dry substrate membrane contacted to the membrane layer following wetting. The fluid in the wetted membrane layer that was used to rehydrate the vitrified materials in the membrane layer is also used to rehydrate the substrate membrane, thereby allowing flow of the substrate from the substrate membrane to a desired target site for improved signal generation. To improve signal and false positives, the substrate may be introduced at a site well upstream of the test site to introduce a substantially linear substrate flow in the membrane as substantially illustrated in FIG. 17C.

To achieve these unique substrate flow characteristics, FIG. 18A-E illustrates various aspects of an exemplary assay device 800 for delayed application of substrate to a membrane layer. A membrane strip includes a sample pad 805 and a conjugate pad 815 disposed next to and/or overlapping with and/or in contact with the sample pad 805. The conjugate pad may include one or more reporters vitrified therein or thereon that will flow to the membrane strip that includes one or more test sites 822 thereon. Downstream of the conjugate pad 815 and fluidically connected thereto, optionally integral therewith, is a membrane strip including one or a plurality of test regions 822, each test region comprising a vitrified immobilized capture agent, the capture agent specific for the type of test analyte (e.g. human IgG, SARS-CoV-2 S protein, etc.) or specific for a control. Optionally, each test region may include a different vitrified capture agent, such as a capture antigen, antibody, aptamer, or the like. A control region 845 is optionally disposed on the membrane strip, optionally downstream of the test regions. In some aspects, the assay further includes a waste pad 850 for absorbing excess fluid from the sample. The housing 860 may be formed of an upper housing 862 and lower housing 863 that fit together to house the membrane strip, but it is appreciated that the upper housing and lower housing may be integral and formed of a single piece. A housing may further include a substrate delivery lever 870 that includes affixed thereto or integral therewith, a substrate pad 875. The substrate pad may be affixed to the substrate delivery lever by any desired means such as an adhesive, optionally a releasable adhesive, or by directly incorporating a membrane suitable for vitrification of a substrate therein into the lever. The substrate pad 875 is positioned on the lever 870 such that actuating the lever will place the substrate pad in contact with a portion of the membrane to rehydrate the substrate and mobilize it for reaction with a reporter.

Continuing to refer to FIG. 18, the lever 870 may fit into a lever slot 881 within the housing 862. The fit between the lever 870 and the lever slot 881 may allow actuation of the lever and contacting of the substrate pad to the membrane strip. In some aspects, a lever includes a screw element or shape that is complementary to a screw element or shape within the lever slot such that rotating the lever will move the substrate pad from a first position to a second position that is in contact with the membrane strip as illustrated in FIG. 18C. In other aspects, a lever 780 may be friction fit into a lever slot 881 such that application of a desired amount of force will move the substrate pad 875 into contact with the membrane strip. It is desired in some aspects to include a system that can be actuated by a user to move the membrane strip from the first position to the second position in contact with the membrane strip at a desired time, but is resistant to accidental movement of the substrate membrane. It is noted that the position of the substrate pad within the housing can be tailored to contact the membrane strip at any desired position. Optionally, as illustrated in FIG. 18B, the lever is positioned to contact the substrate pad 875 to the membrane strip at or near the conjugate pad 815. Alternatively or in addition, the lever is positioned to contact the substrate pad to the membrane strip at or near the sample pad 805. Alternatively or in addition, the lever is positioned to contact the substrate pad to the membrane strip at or near the sample pad test site or any position upstream of the test site such that upon rehydration the substrate may flow by surface capillary action from the substrate pad to the test site(s).

A housing 862 optionally further includes a sample port 880 that is positioned substantially near the sample pad 805 such that a user may readily localize a biological sample to the sample pad. The sample port 880 may further include an assay reagent delivery port 885. The assay reagent delivery port may include vitrified therein one or more assay reagents that may be used to supplement a biological sample or otherwise deliver one or more additives to a membrane strip. Illustrative examples of an assay reagent includes, but is not limited to a buffering agent (e.g. potassium phosphate, HEPES, TRIS, etc.), detergent (e.g. tween, etc.), among many others. A user may take a biological sample, or portion thereof and add it to the delivery port 885 that rehydrates the additives allowing the additive to be combined with the biological sample and improve overall assay or device performance. Optionally, a device includes an assay reagent delivery port. Optionally, a device excludes an assay reagent delivery port.

Continuing to refer to FIG. 18, a device housing may further include a lower housing 863 that includes one or more membrane strip slots 890, 892 to house and maintain the orientation of the membrane strip within the housing. A readout shelf 895 may also be present to maintain the position of the membrane relative to the lower housing and optionally to prevent deflection of the membrane upon actuation of the lever 870 to force the membrane strip into contact with the substrate pad 875 when the lever 870 is actuated.

Figure 18A:
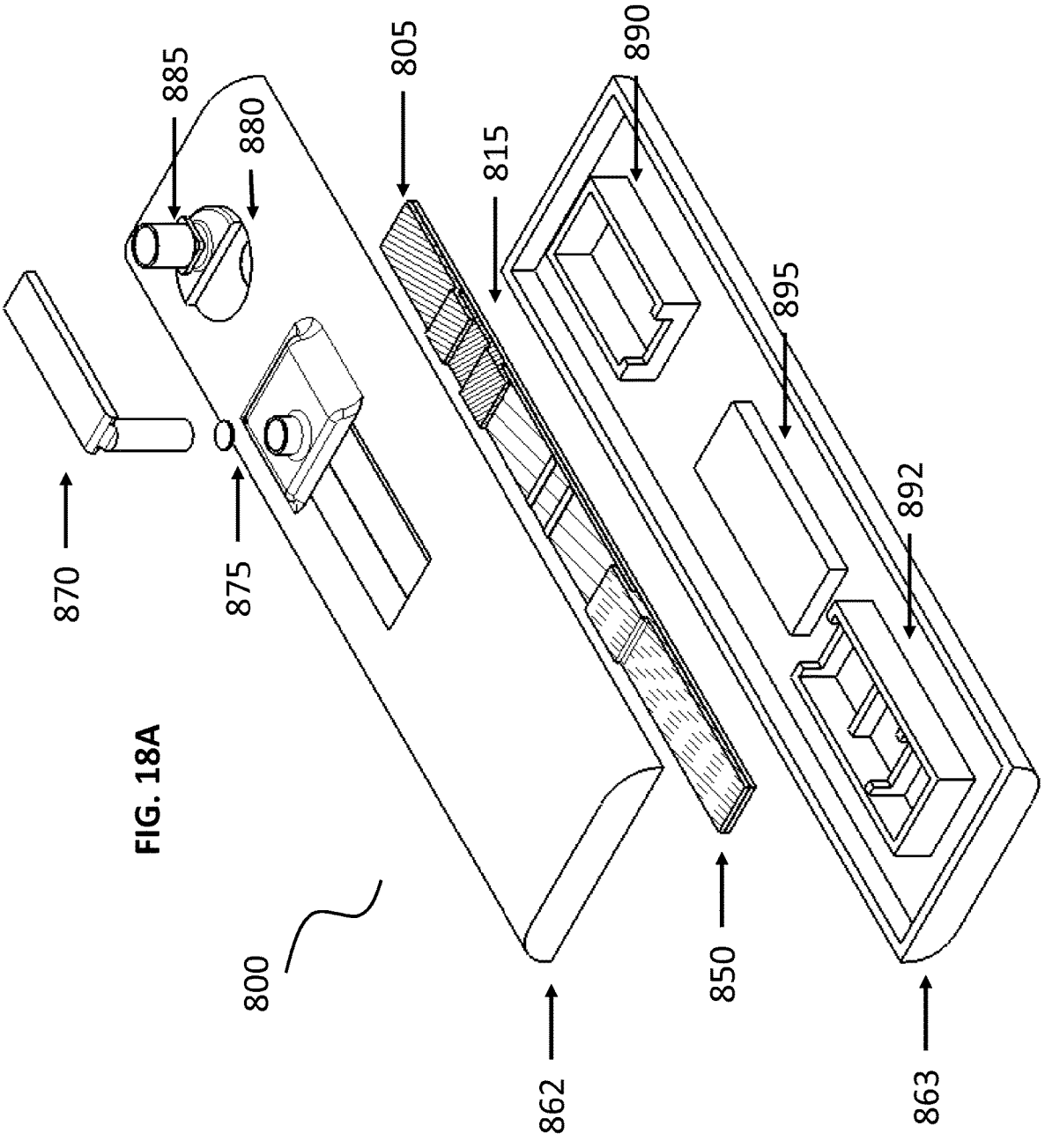
FIG. 18A illustrates a blowup of device according to some aspects as provided herein including a substrate membrane on a lever for application of substrate to a membrane layer.
Figure 18B:
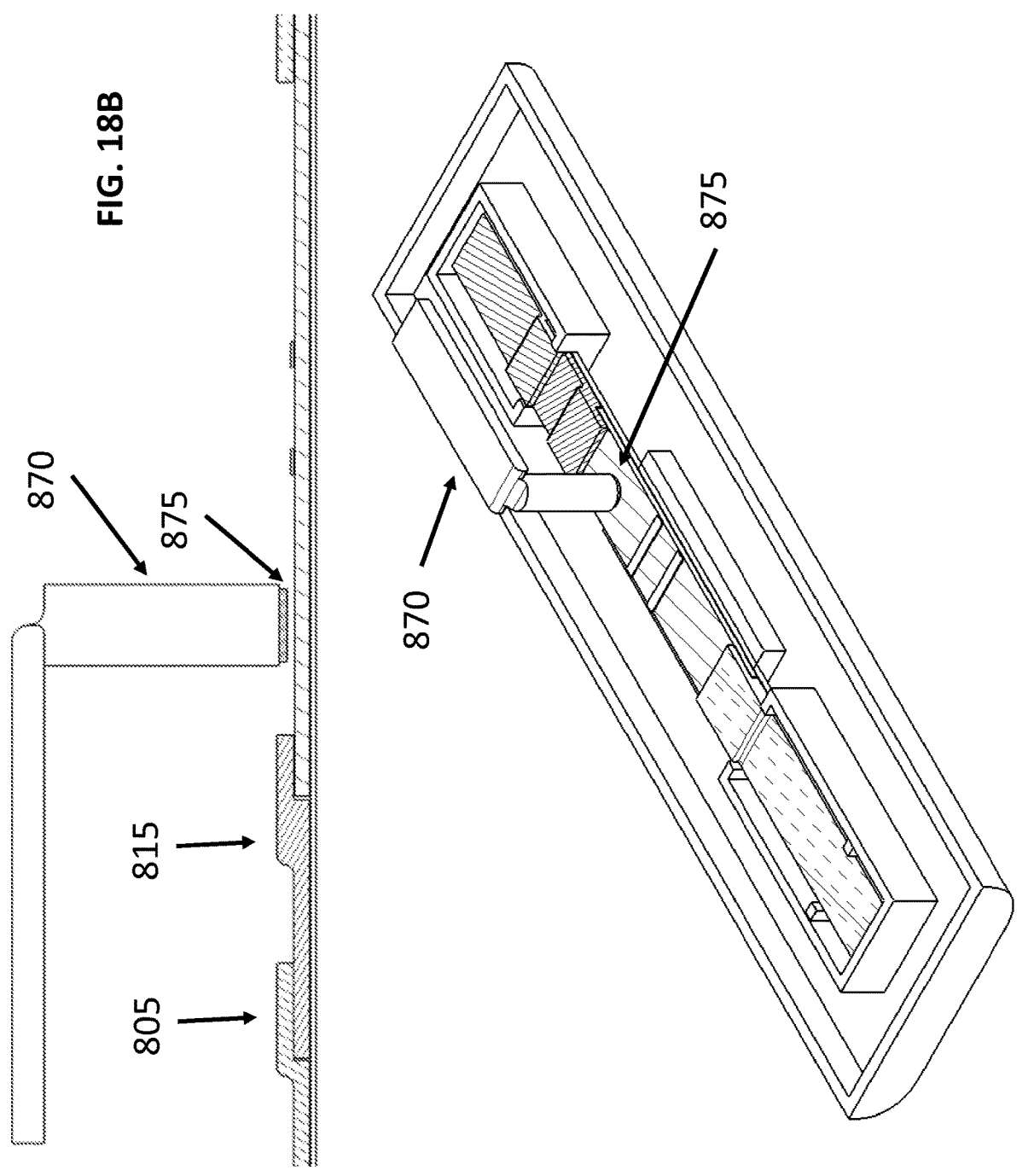
FIG. 18B illustrates the device of FIG. 17A illustrating the position of the substrate membrane and lever relative to a membrane strip according to some aspects.
Figure 18C:
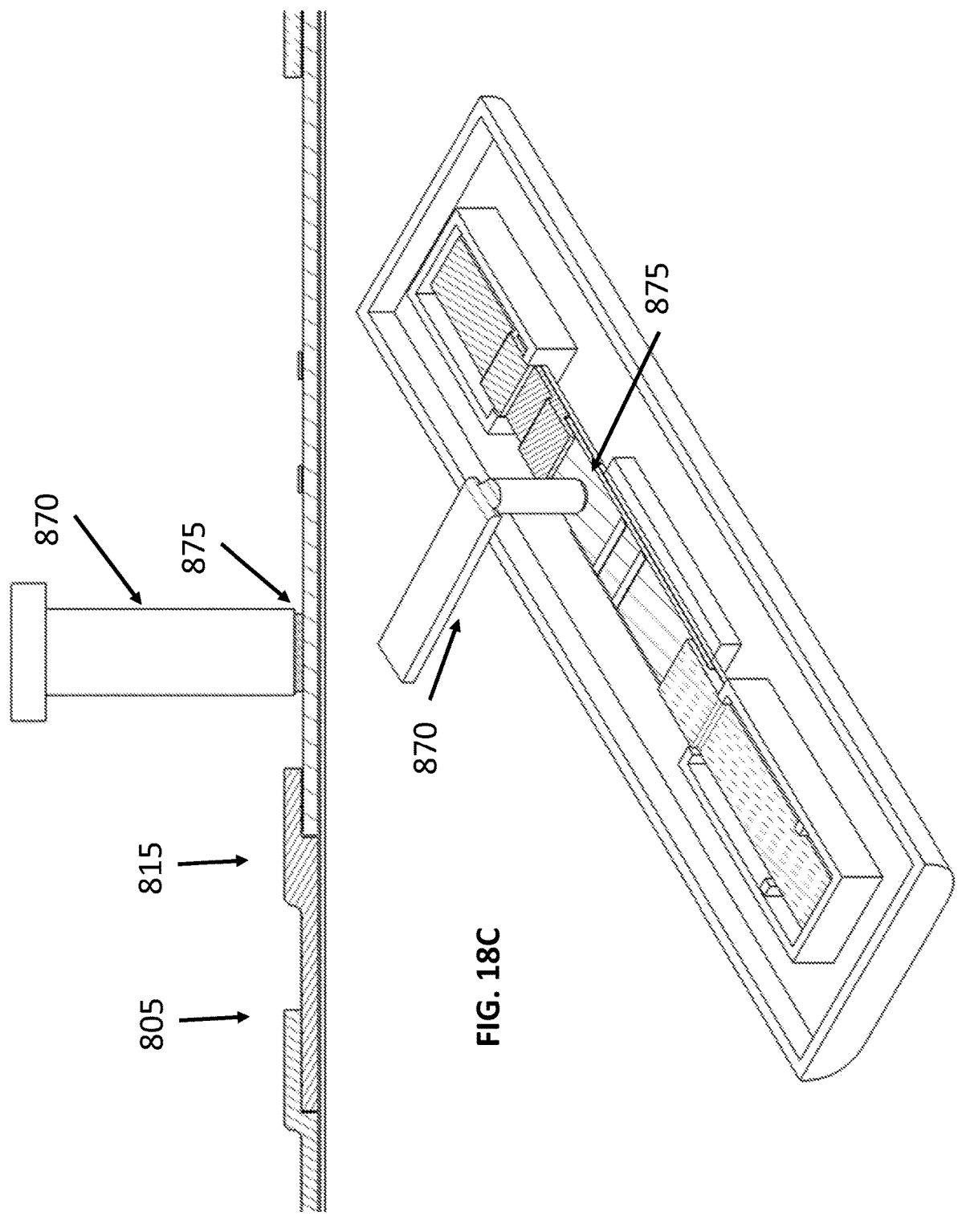
FIG. 18C illustrates the device of FIG. 17A illustrating the position of the substrate membrane and lever relative to a membrane strip according to some aspects when the lever is actuated to promote contact between the membrane strip and the substrate pad.
Figure 18D:
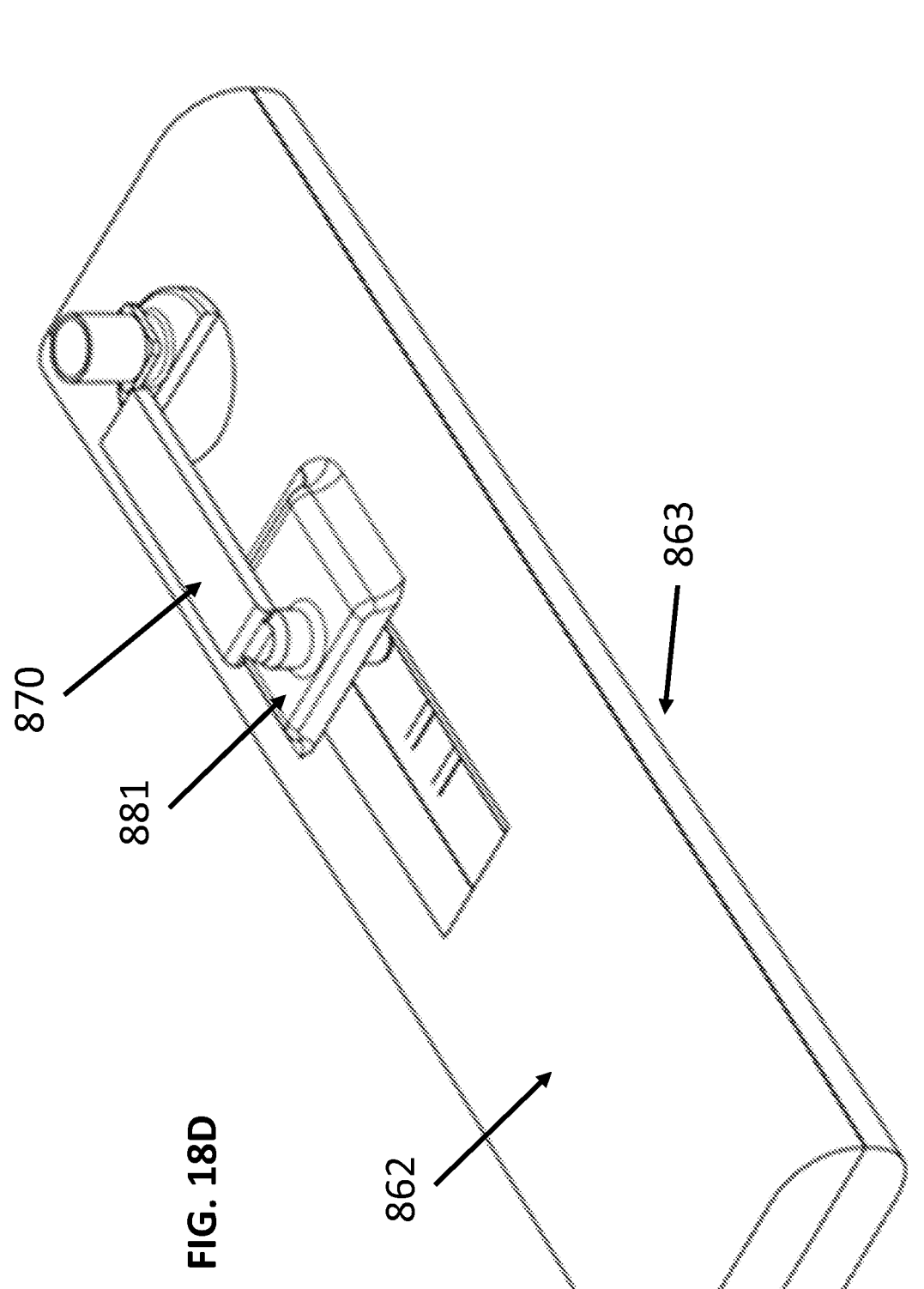
FIG. 18D illustrates a fully assembled exemplary device according to some aspects.
Figure 18E:
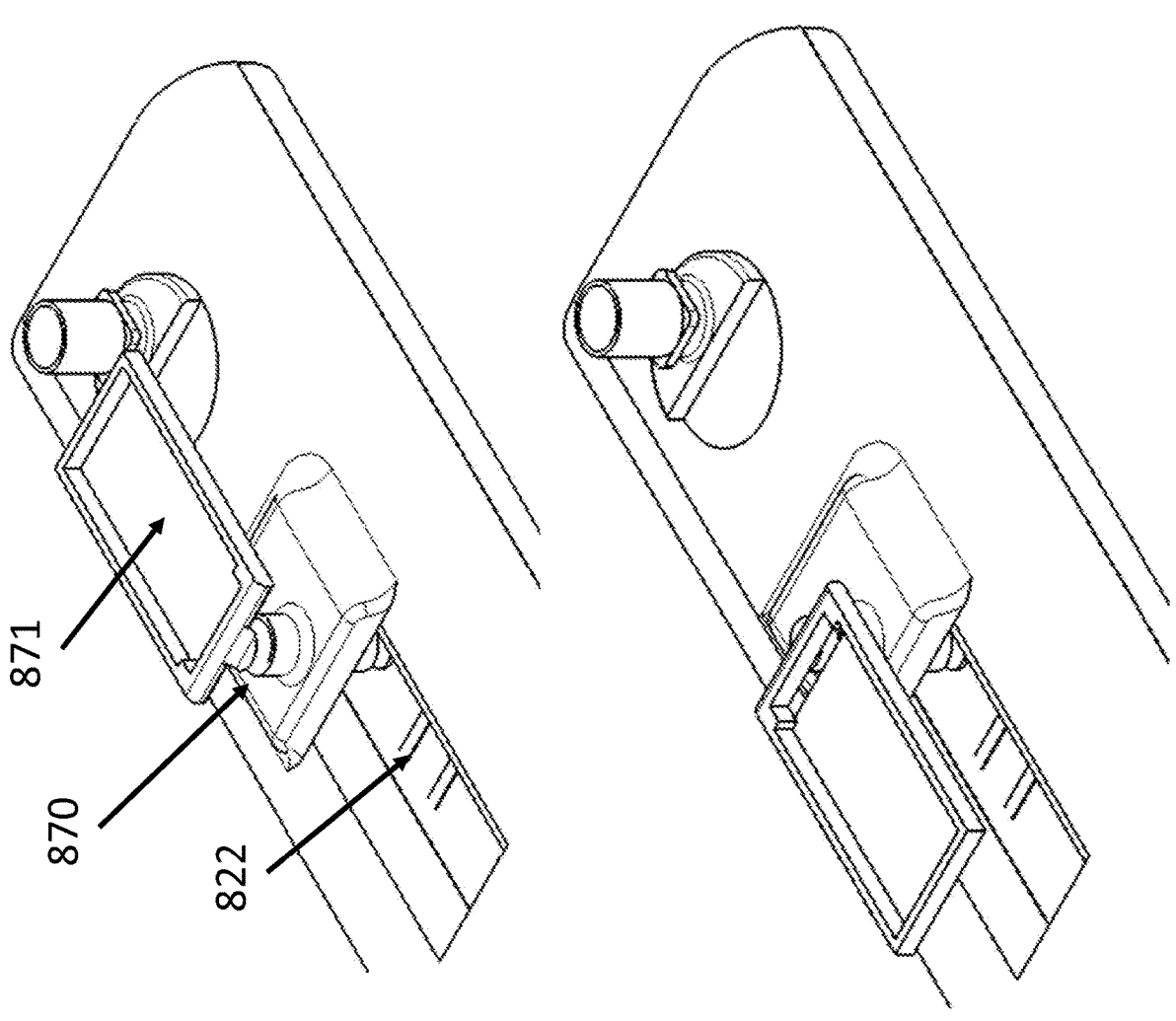
FIG. 18E illustrates another example of a fully assembled exemplary device according to some aspects as provided herein where a lever may be or include a magnifying region.

Referring to FIG. 18E, a lever 870 may include a magnifying region 871 that upon actuation of the lever 870 may rest over the one or more test sites 822 such that readout of the test site may be more easily performed by a user. As is apparent from FIGS. 17C and 17E the amount of rotation of other movement of the lever may be designed such that contact of the sample pad with the membrane strip is achieved at the desired rotational level. Contact of the sample pad to the membrane strip as illustrated in FIG. 17C is approximately 90 degrees. Contact of the sample pad to the membrane strip as illustrated in FIG. 17E is approximately 180 degrees. As such, rotation of a lever may be from any amount from 0 to 180 degrees to affect contact of the substrate pad to the membrane strip.

The devices or processes as provided herein are able to rapidly detect the presence or absence of a target analyte in a fluid biological sample. Optionally, a target analyte is detectable within 30 minutes of application of the liquid biological sample to the device, optionally 25 minutes or less, optionally 10 minutes or less, optionally 15 minutes or less, optionally 10 minutes or less. In some aspects, such as when a substrate is applied to the membrane layer following application of the liquid biological sample, the liquid biological sample is allowed to move through the membrane layer for about 10 to about 20 minutes, optionally about 15 minutes prior to application of the substrate. The substrate may then be applied to contacted to the membrane layer and the detection of the presence or absence of the target analyte may be allowed to develop for about 1 minute to about 10 minutes, optionally about 5 minutes after which a detectable label may be detected either visually or by detection machine. As such, the devices and methods as provided herein are substantially more rapid than prior methods such as ELISA based systems or chemiluminescent based systems.

Various aspects of the present disclosure are illustrated by the following non-limiting examples. The examples are for illustrative purposes and are not a limitation on any practice of the present disclosure. It will be understood that variations and modifications can be made without departing from the spirit and scope of the disclosure. Similar techniques and other techniques known in the art readily translate the examples. Reagents illustrated herein are commercially available, and a person of ordinary skill in the art readily understands where such reagents may be obtained.

EXAMPLES

A sample device is formed substantially as illustrated in FIG. 17A housed in a polymeric housing that includes a sample application port localized over a sample pad, a second reagent port located over an upstream region of the sample pad, and a test site port allowing access to a test site on the membrane strip. The conjugate pad and membrane is made of cellulose nitrate (CN95) from Sartorius, Goettingen, Germany. The sample pad is chopped glass with binder sold as material 8951 from AHLSTROM-MUNKSJÖ, Helsinki, Finland. The absorbent pad, or waste pad, was formed of cotton fiber sold as material 222 from AHLSTROM-MUNKSJÖ, Helsinki, Finland.

The conjugate pad (25 mm×5 mm) is formed using an Automated Lateral Flow Reagent Dispenser (ALFRD) from ClaremontBio, Upland, CA The coating solution dispensing rate is precisely controlled by a syringe pump while the dispenser is translating over nitrocellulose surface. A dispensing volume to translating speed ratio between 0.291 μL/mm to 0.401 μL/mm leads to a ~1 mm width test line. To form the test strip line, first an anti-Fe antibody is coated on the nitrocellulose at desired spot. After the first coated layer is dry, a second anti-nucleocapsid antibody is coated at the same spot. For example, an anti-mouse IgG (Fe specific) antibody produced in goat (M4280-1ML from Sigma Aldrich), 2 mg/mL, is first striped on CN95 with a dispensing rate/translating speed of 0.291 µL/mm. After first layer is dry, a Mouse MAb SARS-CoV/SARS-CoV-2 Nucleocapsid Antibody (SinoBio 40143-MM05), 1 mg/mL with 5% disaccharide is coated on top of the first layer and vitrified according to the teachings of U.S. Pat. No. 10,433,540.

The sample pad (18 mm×5 mm) is pretreated with 2% Casein, 0.5% Tween-20 in PBS and then dried before assembling the device. The waste pad is 21 mm×5 mm and is used as received from the manufacture. The device is formed on a transparent polycarbonate supporting card coated with double sided tape. The sample pad, conjugate pad, and absorption pad are arranged on the tape and covered with a cover exposing desired regions of the device.

For the detection of analyte, a sample solution is prepared containing SARS-CoV-2 (2019-nCoV) S protein (Sino Biological, Chesterbrook, PA) in 1 wt % BSA, 0.1 wt % Tween-20 in phosphate buffered saline. Alternatively, thermally inactivated SARS-CoV-2 (2019-nCoV) (VR1986HK, ATCC) in 0.1 wt % BSA in PBS is used. When the inactive virus is used, viral load of TCID50 $0.625 \times 102$/ml is digested in artificial saliva (960 µl) (Cat. #1700-0304, Pickering Laboratories, Inc.) including 2 wt % zwittergent 3-14 (0.2 g) and 20 mM DTT (20 µl) for 5 minutes before application to the sample pad.

Gold-Ab-HRP conjugates are formed using Anti-Human SARS Coronavirus Nucleoprotein Mouse MAb (40143-MM05, Sino Biologicals) or Anti-Human SARS Coronavirus Nucleoprotein Rabbit Mab (40143-R001, Sino Biologicals). The antibody is first purified to remove any protein additives for stabilization (e.g. BSA), salt as a preservative (e.g. sodium azide), or salt in the storage buffer (e.g. PBS). The antibody is purified using centrifuge method and buffer is replaced by 10 mM potassium phosphate, pH 7.4, with a concentration no less than 1 mg/mL. A sample of antibody conjugated to HRP is intermixed with an equal amount of unabled antibody for conjugation to particles. Antibodies for conjugation are mixed with gold at a ratio of 100 µg Ab/500 µL OD=20 gold and incubating the mixture at room temperature for 30 mins while shaking or rotating. For example, for an Ab-HRP 50%/Ab 50% mixture, 500 µL OD=20 gold is mixed with 50 µg of Ab-HRP and 50 µg of Ab (unlabeled). A blocking solution is added (25 mM borate with 10% BSA, pH 8.0) at 200 µL blocking buffer/500 µL conjugate solution and incubated at room temperature for 30 mins while shaking or rotating. The conjugated material is spun in a centrifuge at 3600 RCF for 10 mins followed by removal of the supernatant. The pellet is resuspended into vitrification matrix containing 25 mM borate with 1% BSA, pH 8.0, 50:50 mM FeSO4-EDTA and 600 mM Trehalose disaccharide, that may then be vitrified onto the sample pad according to the teachings of U.S. Pat. No. 10,433,540.

For test studies, a 30 µL sample is loaded into the sample port of the cassette followed by adding 70 µl of running buffer (1 wt % BSA, 1 wt % Tween-20 in PBS) to a running buffer port located upstream from the sample port over the sample pad. The assay is allowed to progress for 15 min. In some examples, 10 µL substrate TMBM or TMBMX (Moss Bio) is added onto the nitrocellulose test line and allowed to develop for 5 minutes.

Optionally, a substrate is applied by contacting a dry substrate membrane to the membrane strip. A dry substrate pad may be formed by combining 250 mM trehalose, 2.5 mM EDTA, 0.5 wt % PEG, 62.5 µl TMB (substrate) stock, 399.4 µl reconstitution buffer and 5 µl of 30 wt % H2O2. The reconstitution buffer is 0.03 M acteat with 0.4 wt % sodium nitroferricyanide, pH 3.3. The material is dissolved by vortexing and vitrified into a nitrocellulose membrane according to the teachings of U.S. Pat. No. 10,433,540. To apply the substrate, the vitrified substrate membrane is contacted to the membrane strip upstream of the test site.

Figure 20:
FIG. 20 illustrates a device provided according to some aspects as provided herein processed using recombinant SARS-CoV-2 S protein as a sample and detected to less than 1 pg/ml when developed using the substrate TMBMX.
Figure 21:
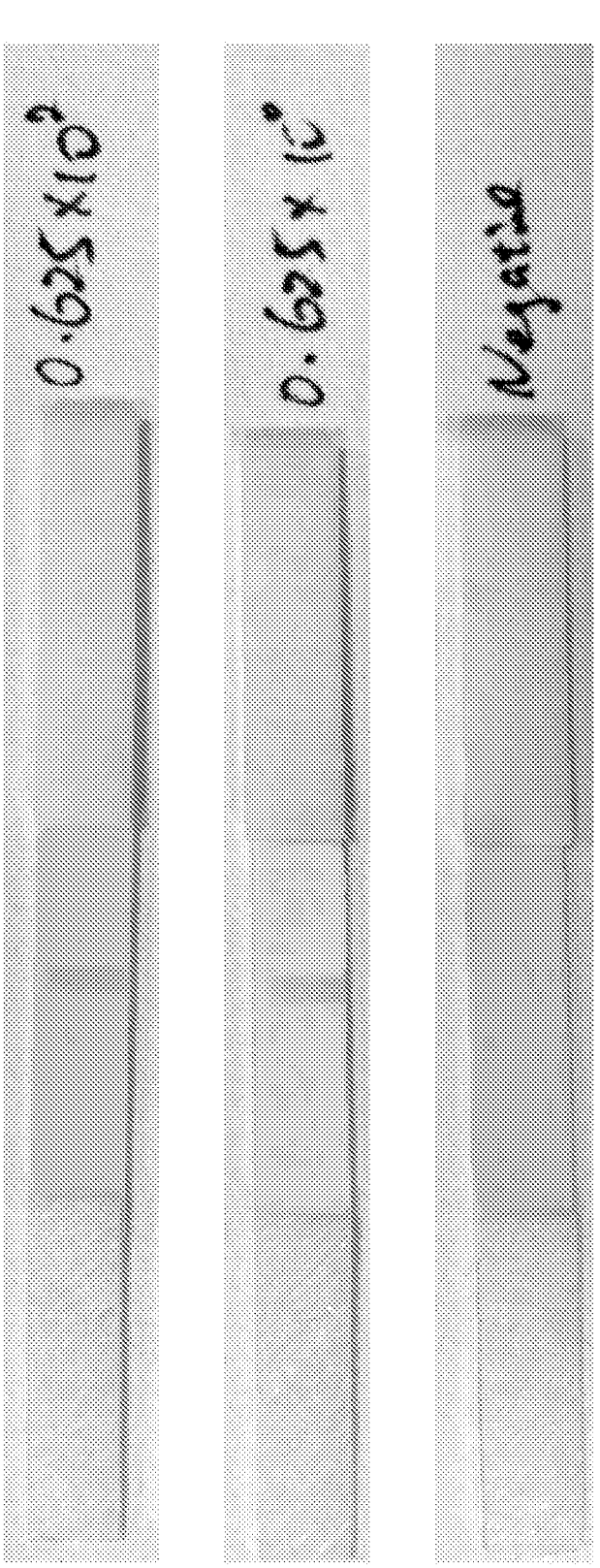
FIG. 21 illustrates a device provided according to some aspects as provided herein processed using thermally inactivated SARS-CoV-2 as a sample and S protein detected at loads of over 100× lower than expected in biological samples when developed using the substrate TMBMX.

Results using isolated are illustrated in FIG. 19 illustrating results using TMBM substrate and FIG. 20 illustrating results using TMBMX substrate and demonstrating that SARS-CoV-2 S protein is detectable in the system to less than 1 µg/ml. Results using inactivated SARS-CoV-2 as a target analyte are illustrated in FIG. 21 demonstrating dilutions at $0.625 \times 102$/ml and $0.625 \times 100$/ml and a negative control illustrating ready detection.

In further studies, a 30 µL sample is loaded into the sample port of the cassette. Vitrified within the sample pad is the material for a running buffer (BSA, Tween-20 in phosphate buffer, sodium salts all at concentrations to yield a running buffer). The running buffer materials are rehydrated by the addition of the sample. The assay is allowed to progress for 15 min. In some examples, 10 µL substrate TMBM or TMBMX (Moss Bio) is added onto the nitrocellulose test line and allowed to develop for 5 minutes. Similar results are expected to be observed.

The same studies were repeated but comparing the binding of capture agent either alone or on top of precoated anti-IgG antibody at a test site. A nitrocellulose membrane strip is striped with 1.5 mg/ml Human SARS Coronavirus Nucleoprotein/NP Ab(40144-MM05, Sino Biological) on top, with 5% sucrose added at a desired target site. SARS-CoV-2 nucleoprotein is diluted in 10× serial dilutions from 1000 ng/ml to zero 1 wt % BSA/0.1 wt % PBST. 30 µl of each diluent along with 0.25 µl of 50 wt % R001+50 wt % R001-HRP conjugated to 40 nm GNP (passive conjugation) was added onto the sample pad. 70 µL of 1 wt % BSA/1 wt % PBST were added as a running buffer to the sample port. The tests run for 20 min. After that 15 µL of TMBMX (Moss) was added to the matrix upstream of the test site. After 5 min, photographs of the resulting test devices were taken with results illustrated in FIG. 22A.

As a comparator, the test site if prepared by coating nitrocellulose CN95 with 2 mg/ml of anti-Mouse IgG (Fe Specific)Ab (M4280, Sigma) first then 1 mg/ml Human SARS Coronavirus Nucleoprotein/NP Ab(40144-MM05, Sino Biological) on top, with 5% sucrose added in each coating layer. The remainder of the tests are performed as above. Results are illustrated in FIG. 22B. Both studies show no positive signal absent substrate addition. The use of pre-coated antibody prior to addition of antibody capture agent reduced the lower limit of detection nearly 10 fold.

Further Examples

1. A rapid diagnostic device comprising:
   a housing; and
   a substantially dry membrane layer within the housing, the membrane layer comprising:
   a first matrix;
   a capture agent vitrified into or onto the first matrix at a first test site;
   optionally at least one reporter vitrified into the first matrix.

2. The device of aspect 1, further comprising a substantially dry substrate membrane, the substrate membrane comprising a substrate vitrified into or onto the substrate membrane, the substrate membrane associated with a housing, optionally on a lever or other device suitable for and configured to be contact the substrate with the membrane layer.

3. The device of aspects 1 or 2 further comprising a screen layer disposed proximal to the membrane layer, optionally contacting the membrane layer, the screen layer comprising:

a second matrix configured to substantially capture a contaminant present in a liquid biological sample when the screen layer is contacted with the liquid biological sample.

4. The device of any one of aspects 1-3 wherein said reporter is present and is vitrified into or onto the first matrix between a sample pad and the first test site.

5. The device of any one of aspects 1-4, wherein the capture agent is covalently bound to the first matrix at said first test site.

6. The device of any aspect as provided herein, wherein the first matrix of the membrane layer comprises nitrocellulose, collagen, polycaprolactone, polylactic acid, poly(lactic-co-glycolic acid), or combinations thereof.

7. The device of any one of aspects 1-6, wherein the capture agent is an antigen comprising a nucleic acid, a protein, a peptide, or fragments thereof.

8. The device of aspect 7, wherein the capture agent comprises a viral coat protein, optionally an influenza coat protein, optionally a coronavirus coat protein, optionally SARS-CoV-2 spike (S) protein, a SARS-CoV-2 nucleocapsid (N) protein, or a fragment thereof.

9. The device of any one of aspects 1-6, wherein the capture agent is an antibody that selectively binds a viral coat protein, optionally SARS-CoV-2 spike (S) protein, a SARS-CoV-2 nucleocapsid (N) protein, or a fragment thereof.

10. The device of any one of aspects 1-9, wherein the at least one reporter comprises an antibody, optionally IgG, IgM, or combinations thereof.

11. The device of any one of aspects 1-10, wherein the at least one reporter comprises a detectable label, an enzyme, or both.

12. The device of any one of aspects 1-11, wherein the reporter is bound to a particle.

13. The device of aspect 12, wherein the particle is a nanoparticle, optionally a nanoshell particle, colloidal gold particle, or combination thereof.

14. The device of aspect 13, wherein the particle is a nanoshell particle comprising a siliconoxide core and a gold shell layer coating the core, wherein the core has a radius and the shell layer has a thickness, optionally where a ratio of the radius to the thickness is 3:1 to 12:1.

15. The device of aspect 12, wherein the reporter is bound to the particle and an enzyme, fluorescent detectable label, luminescent detectable label, radioisotope detectable label, or combination thereof.

16. The device of aspect 12, wherein the reporter is covalently or electrostatically bound to an enzyme, optionally horseradish peroxidase or alkaline phosphatase.

17. The device of any one of aspects 1-16, wherein the reporter further comprises a second antibody that is not bound to an enzyme or detectable label.

18. The device of aspect 17, wherein a ratio of number the reporter to the number of second reporter antibody is 80:20 to 20:80, optionally about 50:50.

19. The device of any one of aspects 1-18, wherein said housing comprises a sample port.

20. The device of aspect 19, wherein said sample port further comprises a vitrified assay reagent.

21. The device of aspect 19, wherein said sample port is located proximal to a first end of said membrane layer, and said first target site is located proximal to a second end of said membrane layer.

22. The device of any one of aspects 1-21 further comprising said substantially dry substrate membrane, said substantially dry substrate membrane positioned in said housing between said sample port and said first test site.

23. The device of aspect 22 wherein said substrate membrane is associated with a lever configured to contact said substrate membrane to said membrane layer by rotational position adjustment.

24. The device of any one of aspects 1-23, wherein said capture agent is an antibody, antigen or aptamer.

25. The device of any one of aspects 1-24 further comprising a removable separator layer disposed between the membrane layer and the screen layer.

26. The device according to any of aspects 1-25, wherein the capture agent is an aptamer specific for a target analyte in a biological sample.

27. The device according to aspects 26, wherein the target analyte comprises a pathogen.

28. The device according to aspect 27, wherein the pathogen comprises a virus, bacteria, or a toxin.

29. The device according to aspect 27, wherein the pathogen is a virus, optionally SARS-CoV-2 or influenza virus.

30. The device according to aspect 26, wherein the capture agent is an aptamer comprising a human ACE2 protein, peptide, or fragment thereof.

31. A method of determining the presence or absence of a target analyte in a liquid biological sample, the method comprising:

providing a device comprising a housing, vitrified membrane layer associated with said housing, said vitrified membrane layer comprising a first matrix and a capture agent covalently or electrostatically bound the first matrix at a first target site;

contacting the device with a liquid biological sample, wherein the liquid biological sample rehydrates the vitrified membrane layer or a portion thereof, whereby the target analyte, if present in the liquid biological sample, binds the capture agent and a reporter; and detecting the presence or absence of the target analyte by the presence or absence of a detectable signal at the first target site.

32. The method of aspect 31 further comprising contacting said rehydrated vitrified membrane layer with a substrate membrane comprising a substrate vitrified into or onto the substrate membrane such that liquid in said rehydrated vitrified membrane layer rehydrates said substrate membrane.

33. The method of aspects 31 or 32 further comprising migrating said substrate from said substrate membrane toward said first target site by surface capillary action.

34. The method of any one of aspects 31-33, wherein said reporter is vitrified into or onto said vitrified membrane layer whereby said step of contacting releases the at least one reporter agent from the first matrix so that said reporter agent is capable of binding said analyte.

35. The method of any one of aspects 31-34, wherein the reporter is an antibody.

36. The method of aspect 35, wherein the antibody comprises a detectable label, optionally an enzyme.

37. The method of aspect 35, wherein the reporter further comprises a second antibody that is not bound to a detectable label.

38. The method of aspect 37, wherein a ratio of number the reporter to the number of second reporter antibody is 80:20 to 20:80, optionally about 50:50.

39. The method of any one of aspects 31-34, wherein the reporter is bound to a particle.

40. The method of aspect 39, wherein the particle is a nanoparticle, optionally a nanoshell particle, colloidal gold particle, or combination thereof.

41. The method of aspect 40, wherein the particle is a nanoshell particle comprising a siliconoxide core and a gold shell layer coating the core, wherein the core has a radius and the shell layer has a thickness, optionally where a ratio of the radius to the thickness is 3:1 to 12:1.

42. The method of any one of aspects 39-41, wherein the reporter is bound to the particle and an enzyme, detectable label, or combination thereof.

43. The method of any one of aspects 31-42, wherein the reporter is covalently bound to a detectable label selected from the group consisting of an enzyme, a fluorophore, or both.

44. The method of any one of aspects 31-43, wherein the liquid biological sample comprises saliva, blood, serum, plasma, bronchoalveolar lavage fluid, sputum, or nasal fluid.

45. The method any one of aspects 31-44 or any other aspect as provided herein, wherein the first matrix of the membrane layer comprises nitrocellulose, collagen, polycaprolactone, polylactic acid, poly(lactic-co-glycolic acid), or combinations thereof.

46. The method any one of aspects 31-45, wherein the capture agent comprises a nucleic acid, a protein, a peptide, or fragments thereof.

47. The method any one of aspects 31-46, wherein the capture agent comprises a viral coat protein, optionally SARS-CoV-2 spike (S) protein, a SARS-CoV-2 nucleocapsid (N) protein, or a fragment thereof.

48. The method any one of aspects 31-47, wherein the at least one reporter comprises a detectable label.

49. The method any one of aspects 31-48, wherein detecting the presence or absence of the target analyte comprises:
   contacting the device with a substrate for the detectable label; and
   detecting a signal produced when the substrate binds the detectable label.

50. The method any one of aspects 31-49, wherein the signal comprises a fluorescent signal or a color change.

51. The method any one of aspects 31-50, wherein the device further comprises a screen layer disposed on the membrane layer, wherein the screen layer is configured to substantially capture a contaminant present in the liquid biological sample.

52. The method according to any one of aspects 31-51, wherein presence or absence of the target analyte is detected in about 20 minutes or less.

The devices and methods described herein are presently representative of exemplary aspects, and not intended as limitations on the scope of the invention. Changes therein and other uses will occur to those skilled in the art. Such changes and other uses can be made without departing from the scope of the invention.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/ or "including" when used in this specification, specify the presence of stated features, regions, integers, steps, operations, elements, and/or components, but do not preclude the presence or addition of one or more other features, regions, integers, steps, operations, elements, components, and/or groups thereof. The term "or a combination thereof" means a combination including at least one of the foregoing elements.

Unless otherwise defined, all terms (including technical and scientific terms) used herein have the same meaning as commonly understood by one of ordinary skill in the art to which this disclosure belongs. It will be further understood that terms such as those defined in commonly used dictionaries, should be interpreted as having a meaning that is consistent with their meaning in the context of the relevant art and the present disclosure, and will not be interpreted in an idealized or overly formal sense unless expressly so defined herein.

Various modifications of the present invention, in addition to those shown and described herein, will be apparent to those skilled in the art of the above description. Such modifications are also intended to fall within the scope of the appended claims.

Patents, publications, and applications mentioned in the specification are indicative of the levels of those skilled in the art to which the invention pertains. These patents, publications, and applications are incorporated herein by reference to the same extent as if each individual patent, publication, or application was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A rapid diagnostic device comprising:
   a housing; and
   a dry membrane layer within the housing, the membrane layer comprising:
      a first matrix; and
      a capture agent vitrified in the form of an amorphous material free of any crystalline structure into or onto the first matrix at a first test site.

2. The device of claim 1, further comprising a dry substrate membrane, the substrate membrane comprising a substrate vitrified into or onto the substrate membrane, the substrate membrane associated with a housing and configured to be contacted with the membrane layer.

3. The device of claim 1 further comprising a screen layer disposed proximal to the membrane layer, the screen layer comprising:
   a second matrix configured to substantially capture a contaminant present in a liquid biological sample when the screen layer is contacted with the liquid biological sample.

4. The device of claim 1 further comprising a reporter vitrified into or onto the first matrix between a sample pad and the first test site.

5. The device of claim 1, wherein the capture agent is covalently or electrostatically bound to the first matrix at said first test site.

6. The device of claim 1, wherein the capture agent comprises a viral coat protein, optionally a SARS-CoV-2 spike(S) protein, a SARS-CoV-2 nucleocapsid (N) protein, or a fragment thereof, or an antibody that selectively binds a viral coat protein, optionally SARS-CoV-2 spike(S) protein, a SARS-CoV-2 nucleocapsid (N) protein, or a fragment thereof.

7. The device of claim 4, wherein the at least one reporter comprises a detectable label, an enzyme, or both.

8. The device of claim 4, wherein the reporter is bound to a particle, selected from the group consisting of a nanoparticle, a nanoshell particle, colloidal gold particle, or combination thereof.

9. The device of claim 8, wherein the particle is a nanoshell particle comprising a siliconoxide core and a gold shell layer coating the core, wherein the core has a radius and the shell layer has a thickness, optionally where a ratio of the radius to the thickness is 3:1 to 12:1.

10. The device of claim 8, wherein the reporter is bound to the particle and an enzyme, detectable label, or combination thereof.

11. The device of claim 8, wherein the reporter further comprises a second reporter that is not bound to an enzyme or detectable label.

12. The device of claim 11, wherein a ratio of number the reporter to the number of second reporter is 80:20 to 20:80.

13. The device of any one of claim 1, wherein said housing comprises a sample port comprising a vitrified assay reagent.

14. The device of claim 13, further comprising a substantially dry substrate membrane, wherein said substrate membrane is associated with a lever configured to contact said substrate membrane to said membrane layer by rotational position adjustment.

15. The device of claim 1 further comprising a removable separator layer disposed between the membrane layer and the screen layer.

16. The device according to 1, wherein the capture agent is an aptamer comprising a human ACE2 protein, peptide, or fragment thereof.

17. A method of determining the presence or absence of a target analyte in a liquid biological sample, the method comprising:

providing a device according to claim 1;

contacting the device with a liquid biological sample, wherein the liquid biological sample rehydrates the substantially dry membrane layer or a portion thereof, whereby a target analyte, if present in the liquid biological sample, binds the capture agent and a reporter; and detecting the presence or absence of the target analyte by the presence or absence of a detectable signal at the first test site.

18. The method of claim 17 further comprising contacting said rehydrated vitrified membrane layer with a substrate membrane comprising a substrate vitrified into or onto the substrate membrane such that liquid in said rehydrated vitrified membrane layer rehydrates said substrate membrane.

19. The method of claim 17, wherein the reporter further comprises a second reporter antibody that is not bound to a detectable label.

20. The method of claim 19, wherein a ratio of number the reporter to the number of second reporter antibody is 80:20 to 20:80.

\*   \*   \*   \*   \*